US008551035B2

(12) United States Patent
Tanaka

(10) Patent No.: US 8,551,035 B2
(45) Date of Patent: Oct. 8, 2013

(54) METHODS AND DEVICES TO ACCELERATE WOUND HEALING IN THORACIC ANASTOMOSIS APPLICATIONS

(71) Applicant: Portaero, Inc., Cupertino, CA (US)

(72) Inventor: Don Tanaka, Saratoga, CA (US)

(73) Assignee: Portaero, Inc., Cupertino, CA (US)

( * ) Notice: Subject to any disclaimer, the term of this patent is extended or adjusted under 35 U.S.C. 154(b) by 0 days.

(21) Appl. No.: 13/673,003

(22) Filed: Nov. 9, 2012

(65) Prior Publication Data

US 2013/0072910 A1 Mar. 21, 2013

Related U.S. Application Data

(63) Continuation of application No. 12/690,294, filed on Jan. 20, 2010, now Pat. No. 8,323,230, and a continuation of application No. 10/881,408, filed on Jun. 30, 2004, now Pat. No. 7,682,332.

(60) Provisional application No. 60/487,412, filed on Jul. 15, 2003.

(51) Int. Cl.
*A61N 1/30* (2006.01)

(52) U.S. Cl.
USPC ............................................. 604/19; 424/443

(58) Field of Classification Search
None
See application file for complete search history.

(56) References Cited

U.S. PATENT DOCUMENTS

2004/0225254 A1* 11/2004 Tanaka et al. .................... 604/58

FOREIGN PATENT DOCUMENTS

| EP | 0260543 A1 | 3/1988 |
| EP | 1358904 | 5/2003 |
| EP | 1658867 | 5/2006 |
| EP | 1815821 | 8/2007 |
| JP | 62-202847 U | 6/1986 |
| JP | 2000197706 | 7/2000 |
| RU | 2192185 | 10/2002 |
| WO | WO96/39960 | 12/1996 |
| WO | WO99/66975 | 12/1999 |
| WO | WO00/76577 A1 | 12/2000 |
| WO | WO01/45568 A1 | 6/2001 |
| WO | WO02/04054 | 1/2002 |
| WO | WO2005070480 | 8/2005 |

OTHER PUBLICATIONS

Sugarmann et al., "Mesh insertion as an aid for pleurodesis", Journal of Cardiovascular Surgery 1996; 37 (Suppl. 1 to No. 6):173-5.
Swallow et al., "Quadriceps strength predicts mortality in patients with moderate to severe chronic obstructive pulmonary disease", Thorax 2007; 62: 115-120.
Symbas et al., "Nontuberculous Pleural Empyema in Adults, The Role of a Modified Eloesser Procedure in Its Management", The Annals of Thoracic Surgery 1971; 12: 69-78.
Takizawa et al., "Computed tomography-guided drainage for large pulmonary bullae", Interactive Cardiovascular and Thoracic Surgery 2004; 3: 283-285.

(Continued)

*Primary Examiner* — Bethany Barham
(74) *Attorney, Agent, or Firm* — Fliesler Meyer LLP

(57) ABSTRACT

A minimally invasive lung reduction device which overcomes the disadvantages associated with treating chronic obstructive pulmonary disease by utilizing the phenomenon of collateral ventilation to increase the expiratory flow from a diseased lung. The device also provides a means for assisting in or facilitating pulmonary decompression to compress the diseased area or area of the lung or lungs to a smaller volume.

16 Claims, 16 Drawing Sheets

(56) References Cited

OTHER PUBLICATIONS

Terry et al., "Collateral Ventilation in Man", The New England Journal of Medicine 1978; 298(1): 10-15.
Thourani et al., "Twenty-six Years of Experience With the Modified Eloesser Flap", Ann Thorac Surg 2003; 76: 401-406.
Toma et al., "Brave new world for interventional bronchoscopy", Thorax 2005; 60: 180-181.
Ugama et al., "Drainage of Giant Bulla with Balloon Catheter Using Chemical Irritant and Fibrin Glue", Chest 1988; 94(6): 1289-1290.
Vainrub et al., "Percutaneous Drainage of Lung Abscess", American Review of Respiratory Disease 1978; 117: 153-160.
Venn et al., "Intracavity drainage for Bulbous, emphysematous lung disease: experience with the Brompton technique", Thorax 1988; 43: 998-1002.
Wood et al., "A multicenter trial of an intrabronchial valve for treatment of severe emphysema", The Journal of Thoracic and Cardiovascular Surgery 2007; 133: 65-73.e2.
Woodring et al., "Pneumothorax ex vacuo", Chest 1996, 110: 1102-1124.
Woolcock et al., "Mechanical factors influencing collateral ventilation in human, dog, and pig lungs", Journal of Applied Physiology 1971, 30: 99-115.
Yellin et al., "Percutaneous Tube Drainage: The Treatment of Choice for Refractory Lung Abscess", The Annals of Thoracic Surgery 1985; 39: 266-270.
Yim et al., "Minimally invasive thoracic surgery: where do we stand now?" Hong Kong Medical Journal 1995; 1: 115-122.
Yim et al., "Early results of endoscopic lung volume reduction for emphysema", The Journal of Thoracic and Cardiovascular Surgery 2004; 127: 1564-1573.
International Search Report for PCT/US/2009/034374 dated Aug. 28, 2009; 13 pages.
International Search Report for PCT/US/2009/034380 dated Sep. 24, 2009; 12 pages.
International Search Report for PCT/US2009/034322 dated Oct. 5, 2009; 14 pages.
International Search Report for PCT/US2009/034406 dated Dec. 2, 2009; 16 pages.
Extended European Search Report dated Jun. 22, 2011 for PCT/US2009034374, 7 pages.
Extended European Search Report dated Jun. 15, 2011 for PCT/US2009034322, 7 pages.
Extended European Search Report dated Sep. 16, 2011 for PCT/US2009034380, 12 pages.

\* cited by examiner

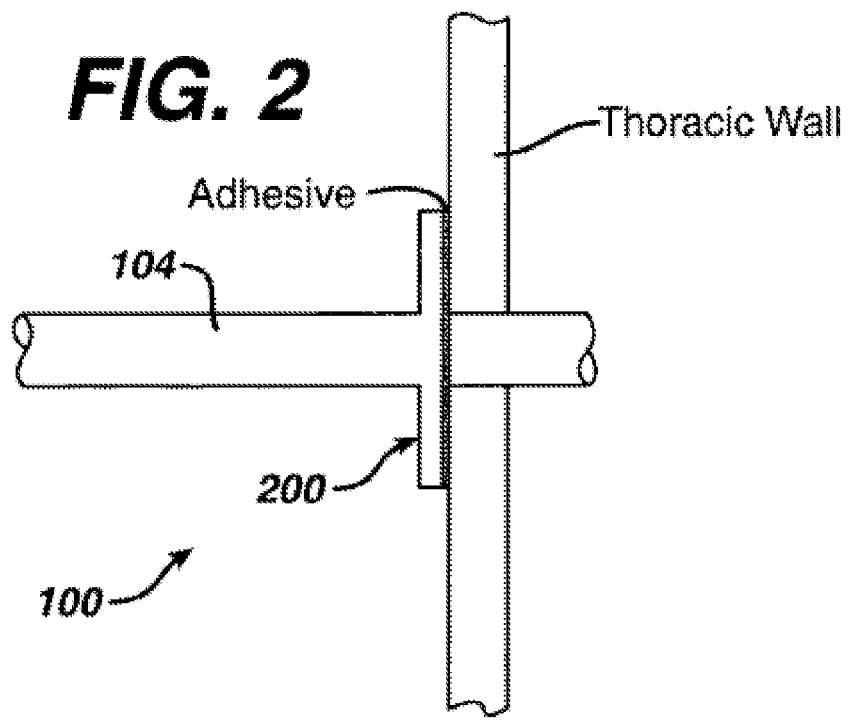
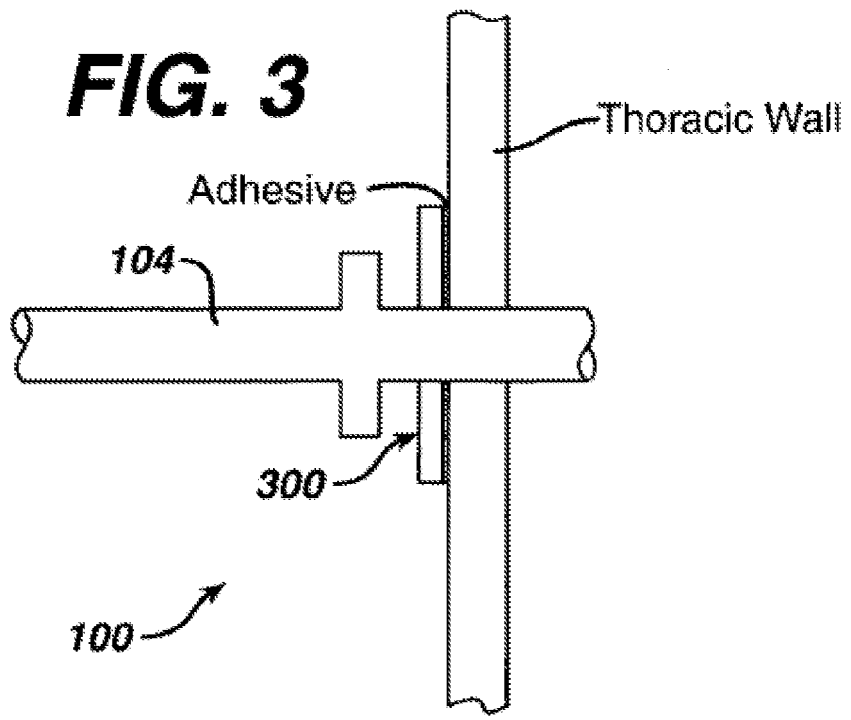

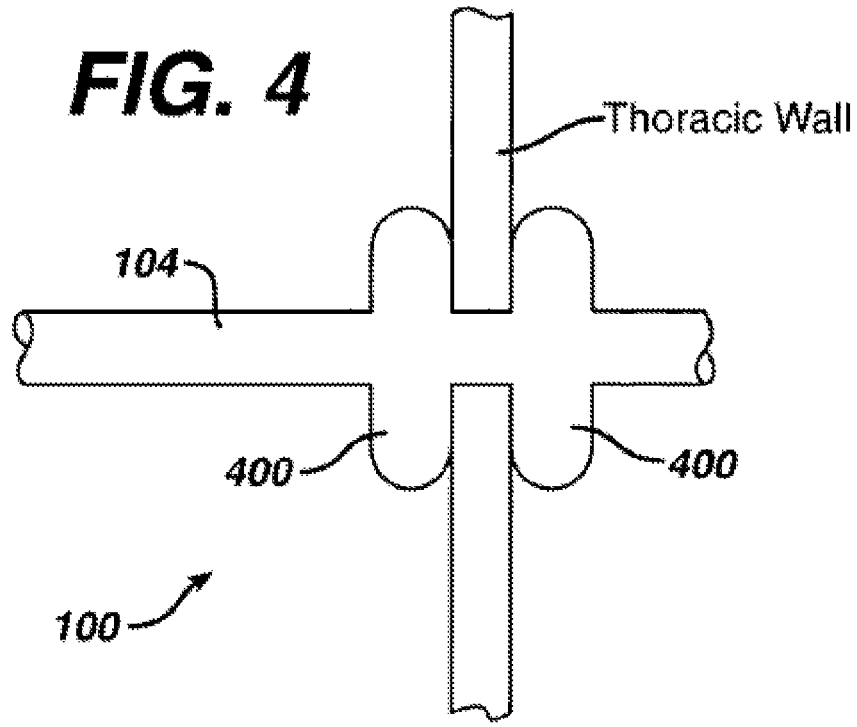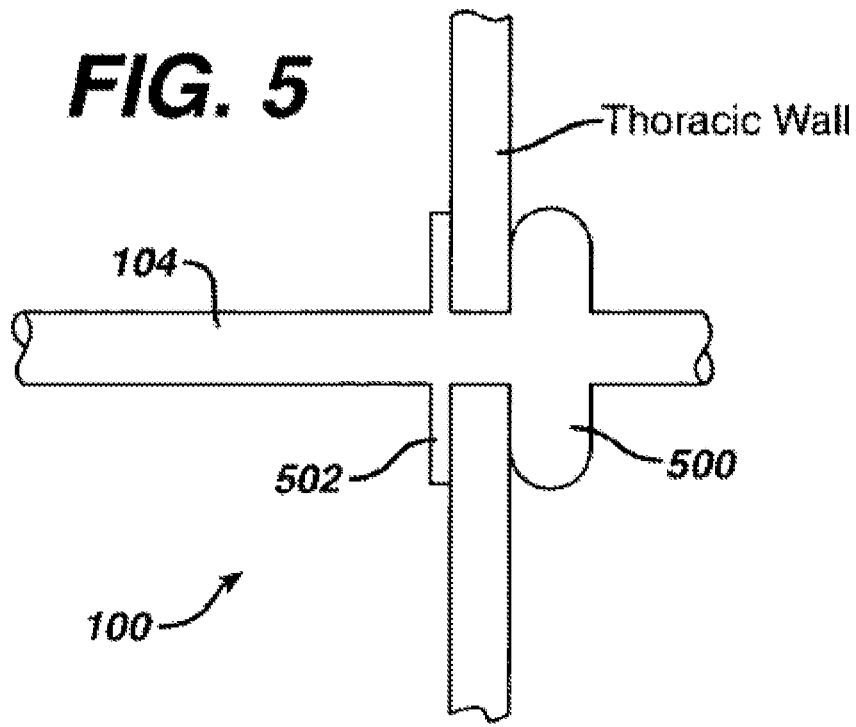

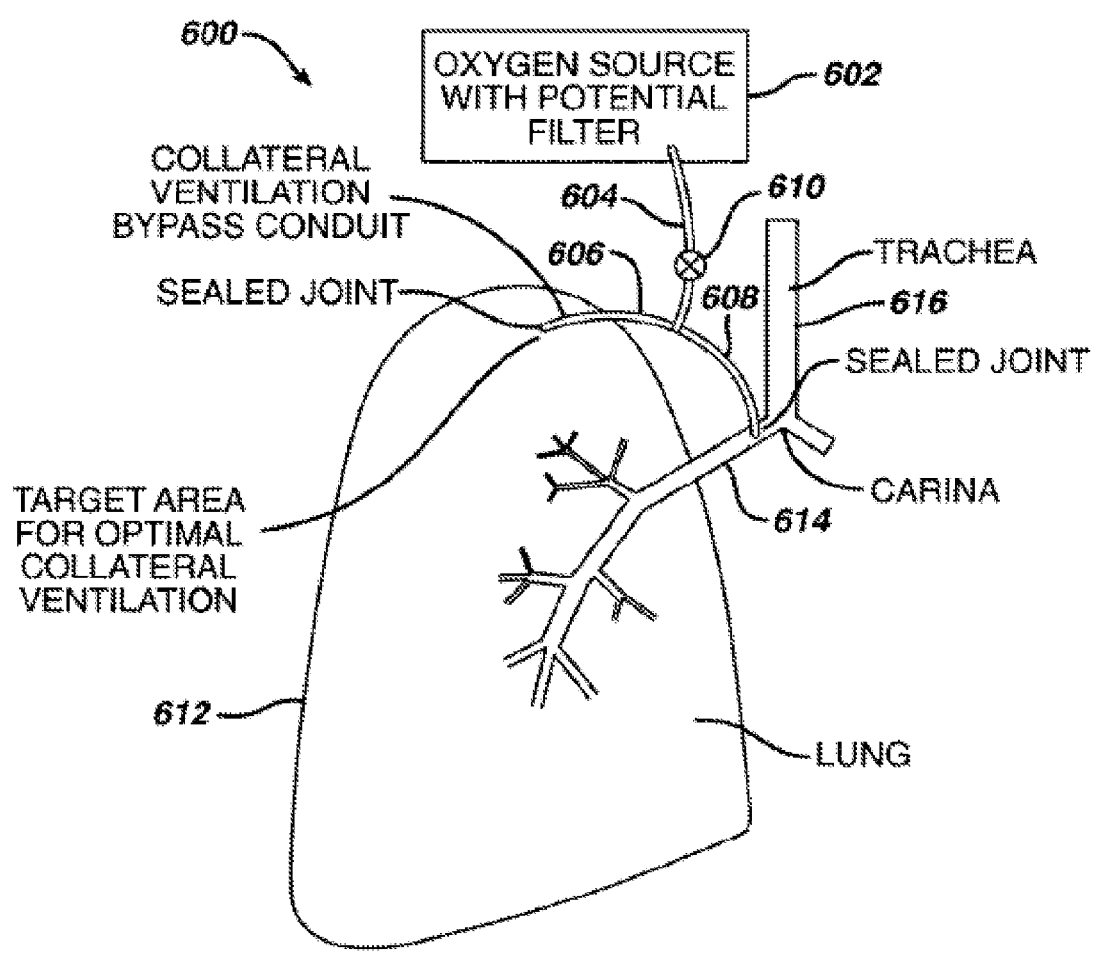

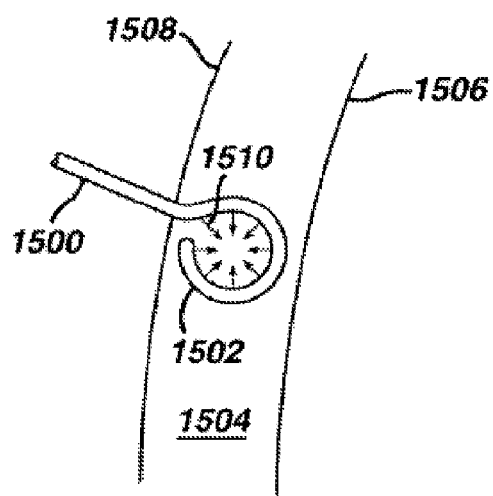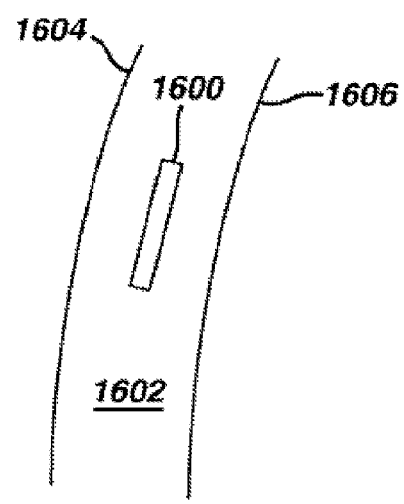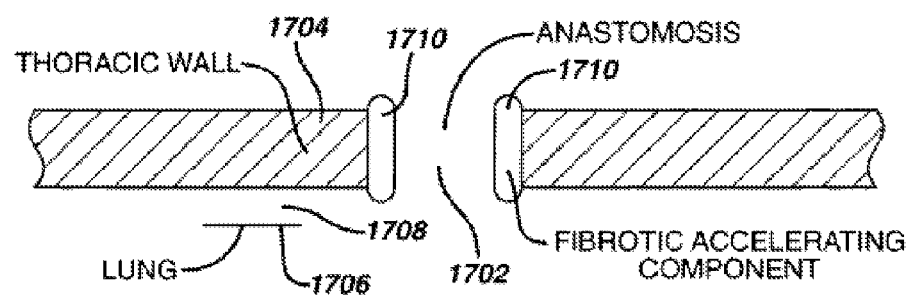

METHODS AND DEVICES TO ACCELERATE WOUND HEALING IN THORACIC ANASTOMOSIS APPLICATIONS

CLAIM TO PRIORITY

This application is a continuation of U.S. patent application Ser. No. 12/690,294, filed Jan. 20, 2010, which is a continuation application of U.S. Pat. No. 7,682,332, issued Mar. 23, 2010 which claims benefit to U.S. Provisional Application No. 60/487,412, filed Jul. 15, 2003. All applications are incorporated by reference herein in their entireties.

BACKGROUND OF THE INVENTION

1. Field of the Invention

The present invention relates to systems and methods for removing trapped air in emphysematous lungs, and more particularly, to systems and methods for removing trapped air in emphysematous hyperinflated lungs by bypassing non-patent airways via a conduit through the outer pleural layer of the lung to a containment/trap device. The present invention also relates to a collateral ventilation bypass system that utilizes the trachea for expelling trapped air rather than a containment/trap device. The present invention also relates to a device and methodology to assist in pulmonary decompression and non-surgical/resection lung volume reduction. The present invention also relates to systems and methods for chemical pleurodesis and systems and methods to accelerate wound healing in thoracic anastomosis applications.

2. Discussion of the Related Art

As a result of studies that date back to the 1930's and particularly studies conducted in the 1960's and early 1970's, it has been determined that long-term continuous oxygen therapy is beneficial in the treatment of hypoxemic patients with chronic obstructive pulmonary disease. In other words, a patient's life and quality of life can be improved by providing a constant supplemental supply of oxygen to the patient's lungs.

However, with the desire to contain medical costs, there is a growing concern that the additional cost of providing continuous oxygen therapy for chronic lung disease will create an excessive increase in the annual cost of oxygen therapy. Thus, it is desirable that oxygen therapy, when provided, be as cost effective as possible.

The standard treatment for patients requiring supplemental oxygen is still to deliver oxygen from an oxygen source by means of a nasal cannula. Such treatment, however, requires a large amount of oxygen, which is wasteful and can cause soreness and irritation to the nose, as well as being potentially aggravating. Other undesirable effects have also been reported. Various other medical approaches, which have been proposed to help reduce the cost of continuous oxygen therapy, have been studied.

Various devices and methods have been devised for performing emergency cricothyroidotomies and for providing a tracheotomy tube so that a patient whose airway is otherwise blocked may continue to breath. Such devices are generally intended only for use with a patient who is not breathing spontaneously and are not suitable for the long term treatment of chronic lung disease. Typically, such devices are installed by puncturing the skin to create a hole into the cricoid membrane of the larynx above the trachea into which a relatively large curved tracheotomy tube is inserted. As previously described, the use of such tubes has been restricted medically to emergency situations where the patient would otherwise suffocate due to the blockage of the airway. Such emergency tracheotomy tubes are not suitable for long term therapy after the airway blockage is removed.

Other devices which have been found satisfactory for emergency or ventilator use are described in U.S. Pat. No. 953,922 to Rogers; U.S. Pat. No. 2,873,742 to Shelden; v3,384,087 to Brummelkamp; U.S. Pat. No. 3,511,243 to Toy; U.S. Pat. No. 3,556,103 to Calhoun; U.S. Pat. No. 2,991,787 to Shelden, et al; U.S. Pat. No. 3,688,773 to Weiss; U.S. Pat. No. 3,817,250 to Weiss, et al.; and U.S. Pat. No. 3,916,903 to Pozzi.

Although tracheotomy tubes are satisfactory for their intended purpose, they are not intended for chronic usage by outpatients as a means for delivering supplemental oxygen to spontaneously breathing patients with chronic obstructive pulmonary disease. Such tracheotomy tubes are generally designed so as to provide the total air supply to the patient for a relatively short period of time. The tracheotomy tubes are generally of rigid or semi-rigid construction and of caliber ranging from 2.5 mm outside diameter in infants to 15 mm outside diameter in adults. They are normally inserted in an operating room as a surgical procedure or during emergency situations, through the cricothyroid membrane where the tissue is less vascular and the possibility of bleeding is reduced. These devices are intended to permit passage of air in both directions until normal breathing has been restored by other means.

Another type of tracheotomy tube is disclosed in Jacobs, U.S. Pat. Nos. 3,682,166 and 3,788,326. The catheter described therein is placed over a 14 or 16-gauge needle and inserted through the cricothyroid membrane for supplying air or oxygen and vacuum on an emergency basis to restore the breathing of a non-breathing patient. The air or oxygen is supplied at 30 to 100 psi for inflation and deflation of the patient's lungs. The Jacobs catheter, like the other tracheotomy tubes previously used, is not suitable for long-term outpatient use, and could not easily be adapted to such use.

Due to the limited functionality of tracheotomy tubes, transtracheal catheters have been proposed and used for long term supplemental oxygen therapy. For example the small diameter transtracheal catheter (16 gauge) developed by Dr. Henry J. Heimlich (described in THE ANNALS OF OTOLOGY, RHINOLOGY & LARYNGOLOGY, November-December 1982; Respiratory Rehabilitation with Transtracheal Oxygen System) has been used by the insertion of a relatively large cutting needle (14 gauge) into the trachea at the mid-point between the cricothyroid membrane and the sternal notch. This catheter size can supply oxygen up to about 3 liters per minute at low pressures, such as 2 psi which may be insufficient for patients who require higher flow rates. It does not, however, lend itself to outpatient use and maintenance, such as periodic removal and cleaning, primarily because the connector between the catheter and the oxygen supply hose is adjacent and against the anterior portion of the trachea and cannot be easily seen and manipulated by the patient. Furthermore, the catheter is not provided with positive means to protect against kinking or collapsing which would prevent its effective use on an outpatient basis. Such a feature is not only desirable but necessary for long term outpatient and home care use. Also, because of its structure, i.e. only one exit opening, the oxygen from the catheter is directed straight down the trachea toward the bifurcation between the bronchi. Because of the normal anatomy of the bronchi wherein the left bronchus is at a more acute angle to the trachea than the right bronchus, more of the oxygen from that catheter tends to be directed into the right bronchus rather than being directed or mixed for more equal utilization by both bronchi. Also, as structured, the oxygen can strike the carina, resulting in an undesirable tickling sensation and cough. In addition, in such devices, if a substantial portion of the oxygen is directed against the back wall of the trachea causing erosion of the mucosa in this area which may cause chapping and bleeding. Overall, because of the limited output from the device, it may not operate to supply sufficient supplemental oxygen when the patient is exercising or otherwise quite active or has severe disease.

Diseases associated with chronic obstructive pulmonary disease include chronic bronchitis and emphysema. One aspect of an emphysematous lung is that the communicating flow of air between neighboring air sacs is much more prevalent as compared to healthy lungs. This phenomenon is known as collateral ventilation. Another aspect of an emphysematous lung is that air cannot be expelled from the native airways due to the loss of tissue elastic recoil and radial support of the airways. Essentially, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen.

Currently, treatments for chronic obstructive pulmonary disease include bronchodilating drugs, oxygen therapy as described above, and lung volume reduction surgery. Bronchodilating drugs only work on a percentage of patients with chronic obstructive pulmonary disease and generally only provides short-term relief. Oxygen therapy is impractical for the reasons described above, and lung volume reduction surgery is an extremely traumatic procedure that involves removing part of the lung. The long term benefits of lung volume reduction surgery are not fully known.

Accordingly, there exists a need for increasing the expiratory flow from an individual suffering from chronic obstructive pulmonary disease. In addition, there exists a need for a minimally invasive means for removing trapped air from the lung or lungs that would allow healthy lung tissue to better ventilate. There also exists a need for a minimally invasive means for allowing trapped air from the lung or lungs to escape that would allow healthy lung tissue to better ventilate. In each of these devices, systems and methods, an opening is created between the lung or lungs and the thoracic wall for placement of conduits or other devices. This opening is essentially an anastomosis. The creation of this anastomosis may present certain difficulties, for example, the potential for infection. Accordingly, there exists a need for minimizing the risk of infection and other complications in the creation of a thoracic anastomosis.

SUMMARY OF THE INVENTION

The present invention overcomes the disadvantages associated with treating chronic obstructive pulmonary disease, as briefly described above, by utilizing the phenomenon of collateral ventilation to increase the expiratory flow from a diseased lung. The present invention also provides a means for assisting in or facilitating pulmonary decompression to compress the diseased area or area of the lung or lungs to a smaller volume. The present invention also overcomes the disadvantages associated with the complications of creating a thoracic anastomosis by accelerating wound healing.

The collateral ventilation bypass systems of the present invention remove trapped air in an emphysematous hyperinflated lung by bypassing non-patent airways via one or more conduits through the outer pleural layer of the lung. Since the thoracic wall must have a passageway there through, there will be newly exposed tissue. Accordingly, the present invention is directed to devices and methods for accelerating wound healing.

In accordance with a first aspect, the present invention is directed to a device for accelerating wound healing in a thoracic anastomosis. The device comprising a fibrosis accelerating component, and a support structure for maintaining the fibrosis accelerating component in contact with at least a portion of the tissue forming the anastomosis.

In accordance with another aspect, the present invention is directed to a device for accelerating wound healing in a thoracic anastomosis. The device comprising a fibrosis accelerating component, a support structure for maintaining the fibrosis accelerating component in contact with at least a portion of the tissue forming the anastomosis, and one or more agents in therapeutic dosages releasably affixed to at least a portion of the fibrosis accelerating component, the one or more agents facilitating wound healing.

In accordance with another aspect, the present invention is directed to a device for accelerating wound healing in a thoracic anastomosis. The device comprising a lattice structure, and at least one element for maintaining the lattice structure in contact with at least a portion of the tissue surrounding the anastomosis.

In accordance with another aspect, the present invention is directed to an apparatus for accelerating wound healing in a thoracic anastomosis. The apparatus comprising a first element positioned on a first side of the anastomosis, a second element positioned on a second side of the anastomosis, at least one component connected to the first and second elements, the at least one component maintaining a predetermined spacing between the first and second elements to create a compressive force on the tissue forming the anastomosis.

In accordance with another aspect, the present invention is directed to an apparatus for accelerating wound healing in a thoracic anastomosis. The apparatus comprising a first element positioned on a first side of the anastomosis, a second element positioned on a second side of the anastomosis, and at least one component connected between the first and second elements, the at least one component drawing the first and second elements towards one another thereby creating a compressive force on the tissue forming the anastomosis.

In accordance with another aspect, the present invention is directed to an apparatus for accelerating wound healing in a thoracic anastomosis. The apparatus comprising a first element positioned on a first side of the anastomosis, a second element positioned on a second side of the anastomosis, at least one component connected to the first and second elements, the at least one component maintaining a predetermined spacing between the first and second elements to create a compressive force on the tissue forming the anastomosis, and one or more agents in therapeutic dosages releasably affixed to at least a portion of at least one of the first and second elements of the one or more agents facilitating wound healing.

In accordance with another aspect, the present invention is directed to a device for accelerating wound healing in a thoracic anastomosis comprising a one-piece structure configured to exert a substantially constant compressive force on the tissue surrounding the anastomosis.

In accordance with another aspect, the present invention is directed to a method for accelerating wound healing in a thoracic anastomosis comprising the promotion of tissue ingrowth through a lattice in contact with the tissue surrounding the anastomosis.

In accordance with another aspect, the present invention is directed to a method for accelerating wound healing in a thoracic anastomosis comprising exerting a substantially constant compression force on the tissue surrounding the anastomosis.

The long-term oxygen therapy system of the present invention delivers oxygen directly to diseased sites in a patient's lungs. Long-term oxygen therapy is widely accepted as the standard treatment for hypoxia caused by chronic obstructive pulmonary disease, for example, pulmonary emphysema. Pulmonary emphysema is a chronic obstructive pulmonary disease wherein the alveoli of the lungs lose their elasticity and the walls between adjacent alveoli are destroyed. As more and more alveoli walls are lost, the air exchange surface area of the lungs is reduced until air exchange becomes seriously impaired. The combination of mucus hypersecretion and dynamic air compression is a mechanism of airflow limitation in chronic obstructive pulmonary disease. Dynamic air compression results from the loss of tethering forces exerted on the airway due to the reduction in lung tissue elasticity. Essentially, stale air accumulates in the lungs, thereby depriving the individual of oxygen. Various methods may be utilized to determine the location or locations of the diseased tissue, for example, computerized axial tomography or CAT scans, magnetic resonance imaging or MRI, positron emission tomograph or PET, and/or standard X-ray imaging. Once the location or locations of the diseased tissue are located, anastomotic openings are made in the thoracic cavity and lung or lungs and one or more oxygen carrying conduits are positioned and sealed therein. The one or more oxygen carrying conduits are connected to an oxygen source, which supplies oxygen under elevated pressure directly to the diseased portion or portions of the lung or lungs. The pressurized oxygen essentially displaces the accumulated air and is thus more easily absorbed by the alveoli tissue. In addition, the long-term oxygen therapy system may be configured in such a way as to provide collateral ventilation bypass in addition to direct oxygen therapy. In this configuration, an additional conduit may be connected between the main conduit and the individual's trachea with the appropriate valve arrangement. In this configuration, stale air may be removed through the trachea when the individual exhales since the trachea is directly linked with the diseased site or sites in the lung via the conduits.

The long-term oxygen therapy system of the present invention improves oxygen transfer efficiency in the lungs thereby reducing oxygen supply requirements, which in turn reduces the patient's medical costs. The system also allows for improved self-image, improved mobility, greater exercise capability and is easily maintained.

The above-described long-term oxygen therapy system may be utilized to effectively treat hypoxia caused by chronic obstructive pulmonary disease; however, other means may be desirable to treat other aspects of the disease. As set forth above, emphysema is distinguished as irreversible damage to lung tissue. The breakdown of lung tissue leads to the reduced ability for the lungs to recoil. The tissue breakdown also leads to the loss of radial support of the airways. Consequently, the loss of elastic recoil of the lung tissue contributes to the inability for individuals with emphysema to exhale completely. The loss of radial support of the airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allow the entrapped air to bypass the native airways and be expelled to a containment system outside of the body.

In an alternate embodiment, the trachea, or other proximal airways, including the bronchus, may be utilized for expelling trapped air rather than a containment/trap device.

The pulmonary decompression device of the present invention removes air from hyperinflated regions of the lung or lungs of a patient by creating a slight pressure differential between the internal volume of the lung and a location external of the lung. An apparatus such as a vacuum fan or pump creates the pressure differential, thereby removing the trapped air and reducing the volume of diseased tissue.

The lung reduction device of the present invention allows trapped air from hyperinflated regions of the lung or lungs of a patient to vent to the external environment through a one-way valve. The valve prevents air from flowing back into the lung or lungs.

In order for the system to be effective, the components of the system are preferably sealed to the lung. Accordingly, the localized pleurodesis chemical delivery system of the present invention is utilized to create a pleurodesis in the area or areas of the lung that are most collaterally ventilated. Various chemicals, agents and/or compounds may be delivered via catheter-based delivery systems or via implantable medical devices. Devices and methods may also be utilized to accelerate wound healing thereby reducing the risk of complications.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 2 is a diagrammatic representation of a first exemplary embodiment of a sealing device utilized in conjunction with the long-term oxygen therapy system of the present invention.

FIG. 3 is a diagrammatic representation of a second exemplary embodiment of a sealing device utilized in conjunction with the long-term oxygen therapy system of the present invention.

FIG. 4 is a diagrammatic representation of a third exemplary embodiment of a sealing device utilized in conjunction with the long-term oxygen therapy system of the present invention.

FIG. 5 is a diagrammatic representation of a fourth exemplary embodiment of a sealing device utilized in conjunction with the long-term oxygen therapy system of the present invention.

FIG. 6 is a diagrammatic representation of a second exemplary embodiment of the long-term oxygen therapy system in accordance with the present invention.

FIG. 15 is a diagrammatic representation of a first exemplary embodiment of a localized pleurodesis chemical delivery system.

FIG. 16 is a diagrammatic representation of a second exemplary embodiment of a localized pleurodesis chemical delivery system.

FIG. 17 is a diagrammatic representation of a first exemplary embodiment of a device for accelerating a fibrotic/wound healing response in accordance with the present invention.

DETAILED DESCRIPTION OF THE PREFERRED EMBODIMENTS

Figure 1:
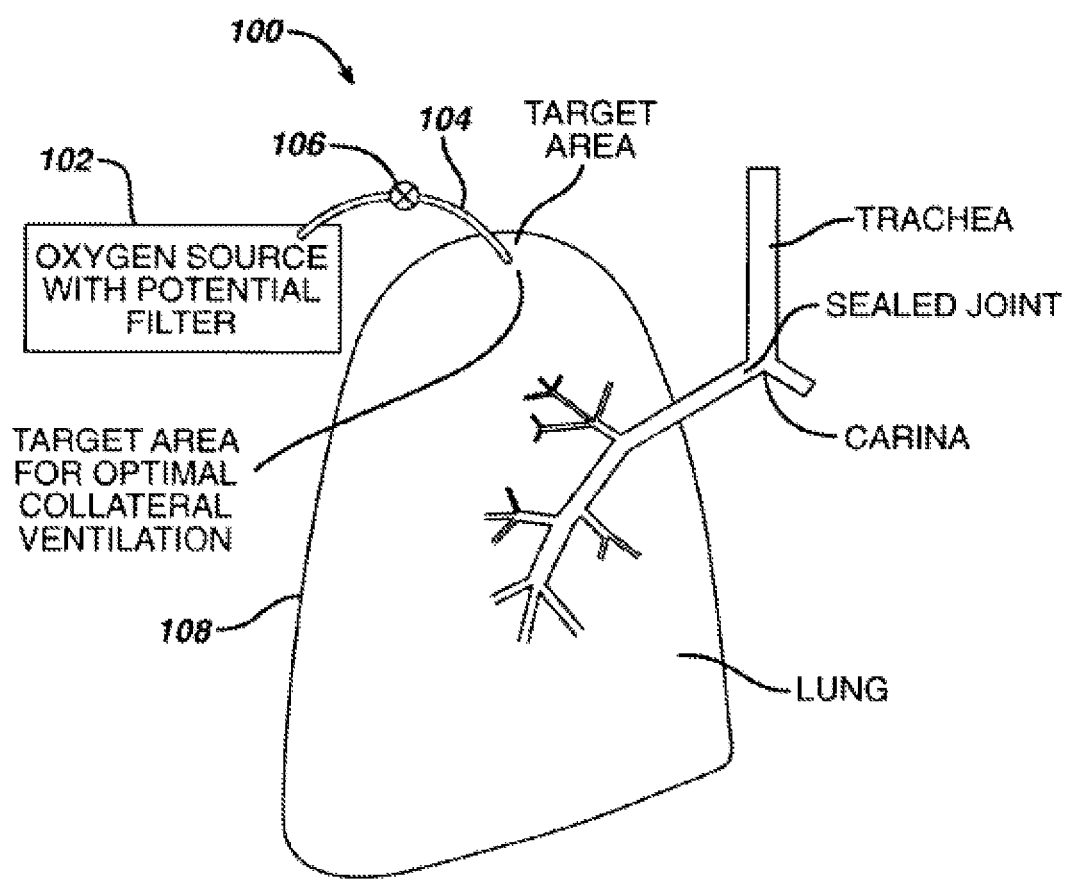
FIG. 1 is a diagrammatic representation of a first exemplary embodiment of the long term oxygen therapy system in accordance with the present invention.

Air typically enters the mammalian body through the nostrils and flows into the nasal cavities. As the air passes through the nostrils and nasal cavities, it is filtered, moistened and raised or lowered to approximately body temperature. The back of the nasal cavities is continuous with the pharynx (throat region); therefore, air may reach the pharynx from the nasal cavities or from the mouth. Accordingly, if equipped, the mammal may breath through its nose or mouth. Generally air from the mouth is not as filtered or temperature regulated as air from the nostrils. The air in the pharynx flows from an opening in the floor of the pharynx and into the larynx (voice box). The epiglottis automatically closes off the larynx during swallowing so that solids and/or liquids enter the esophagus rather than the lower air passageways or airways. From the larynx, the air passes into the trachea, which divides into two branches, referred to as the bronchi. The bronchi are connected to the lungs.

The lungs are large, paired, spongy, elastic organs, which are positioned in the thoracic cavity. The lungs are in contact with the walls of the thoracic cavity. In humans, the right lung comprises three lobes and the left lung comprises two lobes. Lungs are paired in all mammals, but the number of lobes or sections of lungs varies from mammal to mammal Healthy lungs, as discussed below, have a tremendous surface area for gas/air exchange. Both the left and right lung is covered with a pleural membrane. Essentially, the pleural membrane around each lung forms a continuous sac that encloses the lung. A pleural membrane also forms a lining for the thoracic cavity. The space between the pleural membrane forming the lining of the thoracic cavity and the pleural membranes enclosing the lungs is referred to as the pleural cavity. The pleural cavity comprises a film of fluid that serves as a lubricant between the lungs and the chest wall.

In the lungs, the bronchi branch into a multiplicity of smaller vessels referred to as bronchioles. Typically, there are more than one million bronchioles in each lung. Each bronchiole ends in a cluster of extremely small air sacs referred to as alveoli. An extremely thin, single layer of epithelial cells lining each alveolus wall and an extremely thin, single layer of epithelial cells lining the capillary walls separate the air/gas in the alveolus from the blood. Oxygen molecules in higher concentration pass by simple diffusion through the two thin layers from the alveoli into the blood in the pulmonary capillaries. Simultaneously, carbon dioxide molecules in higher concentration pass by simple diffusion through the two thin layers from the blood in the pulmonary capillaries into the alveoli.

Breathing is a mechanical process involving inspiration and expiration. The thoracic cavity is normally a closed system and air cannot enter or leave the lungs except through the trachea. If the chest wall is somehow compromised and air/gas enters the pleural cavity, the lungs will typically collapse. When the volume of the thoracic cavity is increased by the contraction of the diaphragm, the volume of the lungs is also increased. As the volume of the lungs increase, the pressure of the air in the lungs falls slightly below the pressure of the air external to the body (ambient air pressure). Accordingly, as a result of this slight pressure differential, external or ambient air flows through the respiratory passageways described above and fills the lungs until the pressure equalizes. This process is inspiration. When the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. This process is expiration.

Continued insult to the respiratory system may result in various diseases, for example, chronic obstructive pulmonary disease. Chronic obstructive pulmonary disease is a persistent obstruction of the airways caused by chronic bronchitis and pulmonary emphysema. In the United States alone, approximately fourteen million people suffer from some form of chronic obstructive pulmonary disease and it is in the top ten leading causes of death.

Chronic bronchitis and acute bronchitis share certain similar characteristics; however, they are distinct diseases. Both chronic and acute bronchitis involve inflammation and constriction of the bronchial tubes and the bronchioles; however, acute bronchitis is generally associated with a viral and/or bacterial infection and its duration is typically much shorter than chronic bronchitis. In chronic bronchitis, the bronchial tubes secrete too much mucus as part of the body's defensive mechanisms to inhaled foreign substances. Mucus membranes comprising ciliated cells (hair like structures) line the trachea and bronchi. The ciliated cells or cilia continuously push or sweep the mucus secreted from the mucus membranes in a direction away from the lungs and into the pharynx, where it is periodically swallowed. This sweeping action of the cilia, functions to keep foreign matter from reaching the lungs. Foreign matter that is not filtered by the nose and larynx, as described above, becomes trapped in the mucus and is propelled by the cilia into the pharynx. When too much mucus is secreted, the ciliated cells may become damaged, leading to a decrease in the efficiency of the cilia to sweep the bronchial tubes and trachea of the mucus containing the foreign matter. This in turn causes the bronchioles to become constricted and inflamed and the individual becomes short of breath. In addition, the individual will develop a chronic cough as a means of attempting to clear the airways of excess mucus.

Individuals who suffer from chronic bronchitis may develop pulmonary emphysema. Pulmonary emphysema is a disease in which the alveoli walls, which are normally fairly rigid structures, are destroyed. The destruction of the alveoli walls is irreversible. Pulmonary emphysema may be caused by a number of factors, including chronic bronchitis, long term exposure to inhaled irritants, e.g. air pollution, which damage the cilia, enzyme deficiencies and other pathological conditions. In pulmonary emphysema, the alveoli of the lungs lose their elasticity, and eventually the walls between adjacent alveoli are destroyed. Accordingly, as more and more alveoli walls are lost, the air exchange (oxygen and carbon dioxide) surface area of the lungs is reduced until air exchange becomes seriously impaired. The combination of mucus hypersecretion and dynamic airway compression are mechanisms of airflow limitation in chronic obstructive pulmonary disease. Dynamic airway compression results from the loss of tethering forces exerted on the airway due to the reduction in lung tissue elasticity. Mucus hypersecretion is described above with respect to bronchitis. In other words, the breakdown of lung tissue leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen. There is no cure for pulmonary emphysema, only various treatments, including exercise, drug therapy, such as bronchodilating agents, lung volume reduction surgery and long term oxygen therapy.

As described above, long-term oxygen therapy is widely accepted as the standard treatment for hypoxia caused by chronic obstructive pulmonary disease. Typically, oxygen therapy is prescribed using a nasal cannula. There are disadvantages associated with using the nasal cannula. One disadvantage associated with utilizing nasal cannula is the significant loss of oxygen between the cannula and the nose, which in turn equates to more frequent changes in the oxygen source, or higher energy requirements to generate more oxygen. Another disadvantage associated with utilizing nasal cannula is the fact that the cannulas may cause the nasal passages to become dry, cracked and sore.

Transtracheal oxygen therapy has become a viable alternative to long term oxygen therapy. Transtracheal oxygen therapy delivers oxygen directly to the lungs using a catheter that is placed through and down the trachea. Due to the direct nature of the oxygen delivery, a number of advantages are achieved. These advantages include lower oxygen requirements due to greater efficiency, increased mobility, greater exercise capability and improved self-image.

The long term oxygen therapy system and method of the present invention may be utilized to deliver oxygen directly into the lung tissue in order to optimize oxygen transfer efficiency in the lungs. In other words, improved efficiency may be achieved if oxygen were to be delivered directly into the alveolar tissue in the lungs. In emphysema, alveoli walls are destroyed, thereby causing a decrease in air exchange surface area. As more alveoli walls are destroyed, collateral ventilation resistance is lowered. In other words, pulmonary emphysema causes an increase in collateral ventilation and to a certain extent, chronic bronchitis also causes an increase in collateral ventilation. Essentially, in an emphysematous lung, the communicating flow of air between neighboring air sacs (alveoli), known as collateral ventilation, is much more prevalent as compared to a normal lung. Since air cannot be expelled from the native airways due to the loss of tissue elastic recoil and radial support of the airways (dynamic collapse during exhalation), the increase in collateral ventilation does not significantly assist an individual in breathing. The individual develops dsypnea. Accordingly, if it can be determined where collateral ventilation is occurring, then the diseased lung tissue may be isolated and the oxygen delivered to this precise location or locations. Various methods may be utilized to determine the diseased tissue locations, for example, computerized axial tomography or CAT scans, magnetic resonance imaging or MRI, positron emission tomograph or PET, and/or standard X-ray imaging. Once the diseased tissue is located, pressurized oxygen may be directly delivered to these diseased areas and more effectively and efficiently forced into the lung tissue for air exchange.

FIG. 1 illustrates a first exemplary long-term oxygen therapy system 100. The system 100 comprises an oxygen source 102, an oxygen carrying conduit 104 and a one-way valve 106. The oxygen source 102 may comprise any suitable device for supplying filtered oxygen under adjustably regulated pressures and flow rates, including pressurized oxygen tanks, liquid oxygen reservoirs, oxygen concentrators and the associated devices for controlling pressure and flow rate e.g. regulators. The oxygen carrying conduit 104 may comprise any suitable biocompatible tubing having a high resistance to damage caused by continuous oxygen exposure. The oxygen carrying conduit 104 comprises tubing having an inside diameter in the range from about 1/16 inch to about 1/2 inch and more preferably from about 1/8 inch to about 1/4 inch. The one-way valve 106 may comprise any suitable, in-line mechanical valve which allows oxygen to flow into the lungs 108 through the oxygen carrying conduit 104, but not from the lungs 108 back into the oxygen source 102. For example, a simple check valve may be utilized. As illustrated in FIG. 1, the oxygen carrying conduit 104 passes through the lung 108 at the site determined to have the highest degree of collateral ventilation.

The exemplary system 100 described above may be modified in a number of ways, including the use of an in-line filter. In this exemplary embodiment, both oxygen and air may flow through the system. In other words, during inhalation, oxygen is delivered to the lungs through the oxygen carrying conduit 104 and during exhalation, air from the lungs flow through the oxygen carrying conduit 104. The in-line filter would trap mucus and other contaminants, thereby preventing a blockage in the oxygen source 102. In this exemplary embodiment, no valve 106 would be utilized. The flow of oxygen into the lungs and the flow of air from the lungs is based on pressure differentials.

In order for the exemplary long-term oxygen therapy system 100 to function, an airtight seal is preferably maintained where the oxygen carrying conduit 104 passes through the thoracic cavity and lung. This seal is maintained in order to sustain the inflation/functionality of the lungs. If the seal is breached, air can enter the cavity and cause the lungs to collapse as described above.

A method to create this seal comprises forming adhesions between the visceral pleura of the lung and the inner wall of the thoracic cavity. This may be achieved using either chemical methods, including irritants such as doxycycline and/or bleomycin, surgical methods, including pleurectomy or horoscope talc pleurodesis, or radiotherapy methods, including radioactive gold or external radiation. All of these methods are known in the relevant art for creating pleurodesis. With a seal created at the site for the ventilation bypass, an intervention may be safely performed without the danger of creating a pneumothorax of the lung.

Similarly to ostomy pouches or bags, the oxygen carrying conduit 104 may be sealed to the skin at the site of the ventilation bypass. In one exemplary embodiment, illustrated in FIG. 2, the oxygen carrying conduit 104 may be sealed to the skin of the thoracic wall utilizing an adhesive. As illustrated, the oxygen carrying conduit 104 comprises a flange 200 having a biocompatible adhesive coating on the skin contacting surface. The biocompatible adhesive would provide a fluid tight seal between the flange 200 and the skin or epidermis of the thoracic wall. In a preferred embodiment, the biocompatible adhesive provides a temporary fluid tight seal such that the oxygen carrying conduit 104 may be disconnected from the ventilation bypass site. This would allow for the site to be cleaned and for the long term oxygen therapy system 100 to undergo periodic maintenance.

FIG. 3 illustrates another exemplary embodiment for sealing the oxygen carrying conduit 104 to the skin of the thoracic wall at the site of the ventilation bypass. In this exemplary embodiment, a coupling plate 300 is sealed to the skin at the site of the ventilation bypass by a biocompatible adhesive coating or any other suitable means. The oxygen carrying conduit 104 is then connected to the coupling plate 300 by any suitable means, including threaded couplings and locking rings. The exemplary embodiment also allows for cleaning of the site and maintenance of the system 100.

FIG. 4 illustrates yet another exemplary embodiment for sealing the oxygen carrying conduit 104 to the skin of the thoracic wall at the site of the ventilation bypass. In this exemplary embodiment, balloon flanges 400 may be utilized to create the seal. The balloon flanges 400 may be attached to the oxygen carrying conduit 104 such that in the deflated state, the oxygen carrying conduit 104 and one of the balloon flanges passes through the ventilation bypass anastomosis. The balloon flanges 400 are spaced apart a sufficient distance such that the balloon flanges remain on opposite sides of the thoracic wall. When inflated, the balloons expand and form a fluid tight seal by sandwiching the thoracic wall. Once again, this exemplary embodiment allows for easy removal of the oxygen carrying conduit 104.

FIG. 5 illustrates yet another exemplary embodiment for sealing the oxygen carrying conduit 104 to the skin of the thoracic wall at the site of the ventilation bypass. In this exemplary embodiment, a single balloon flange 500 is utilized in combination with a fixed flange 502. The balloon flange 500 is connected to the oxygen carrying conduit 104 in the same manner as described above. In this exemplary embodiment, the balloon flange 500, when inflated, forms the fluid tight seal. The fixed flange 502, which is maintained against the skin of the thoracic wall, provides the structural support against which the balloon exerts pressure to form the seal.

If an individual has difficulty exhaling and requires additional oxygen, collateral ventilation bypass may be combined with direct oxygen therapy. FIG. 6 illustrates an exemplary embodiment of a collateral ventilation bypass/direct oxygen therapy system 600. The system 600 comprises an oxygen source 602, an oxygen carrying conduit 604 having two branches 606 and 608, and a control valve 610. The oxygen source 602 and oxygen carrying conduit 604 may comprise components similar to the above-described exemplary embodiment illustrated in FIG. 1. In this exemplary embodiment, when the individual inhales, the valve 610 is open and oxygen flows into the lung 612 and into the bronchial tube 614. In an alternate exemplary embodiment, the branch 608 may be connected to the trachea 614. Accordingly, during inhalation oxygen flows to the diseased site in the lung or lungs and to other parts of the lung through the normal bronchial passages. During exhalation, the valve 610 is closed so that no oxygen is delivered and air in the diseased portion of the lung may flow from the lung 612, through one branch 606 and into the second branch 608 and finally into the bronchial tube 616. In this manner, stale air is removed and oxygen is directly delivered. Once again, as described above, the flow of oxygen and air is regulated by simple pressure differentials.

The connection and sealing of the oxygen carrying conduit 604 and branches 606, 608 to the lung 612 and bronchial tube 614 may be made in a manner similar to that described above.

The above-described long-term oxygen therapy system may be utilized to effectively treat hypoxia caused by chronic obstructive pulmonary disease; however, other means may be desirable to treat other aspects of the disease. As set forth above, emphysema is distinguished as irreversible damage to lung tissue. The breakdown of lung tissue leads to the reduced ability for the lungs to recoil. The tissue breakdown also leads to the loss of radial support of the native airways. Consequently, the loss of elastic recoil of the lung tissue contributes to the inability for individuals with emphysema to exhale completely. The loss of radial support of the native airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allows the entrapped air to bypass the native airways and be expelled to a containment system outside of the body.

Figure 7:
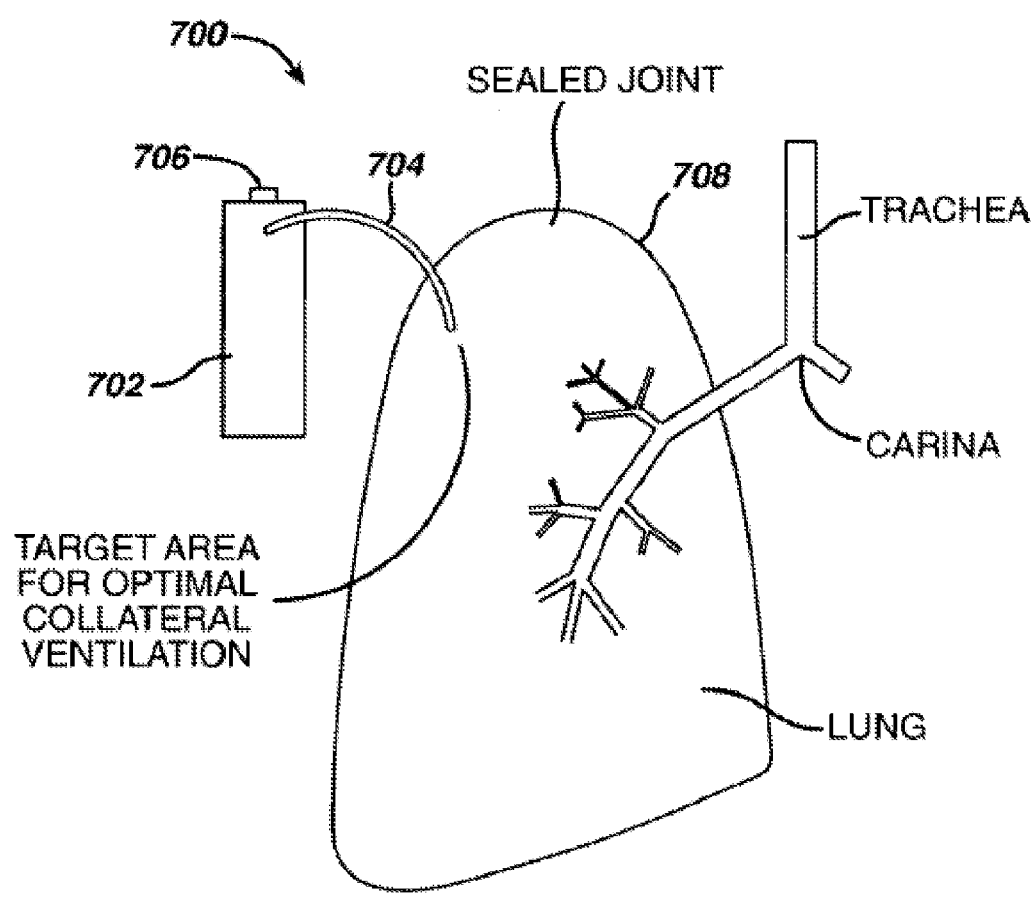
FIG. 7 is a diagrammatic representation of a first exemplary embodiment of a collateral ventilation bypass trap system in accordance with the present invention.

FIG. 7 illustrates a first exemplary collateral ventilation bypass trap system 700. The system 700 comprises a trap 702, an air carrying conduit 704 and a filter/one-way valve 706. The air carrying conduit 704 creates a fluid communication between an individual's lung 708 and the trap 702 through the filter/one-way valve 706. It is important to note that although a single conduit 704 is illustrated, multiple conduits may be utilized in each lung 708 if it is determined that there is more than one area of high collateral ventilation.

The trap 702 may comprise any suitable device for collecting discharge from the individual's lung or lungs 708. Essentially, the trap 702 is simply a containment vessel for temporarily storing discharge from the lungs, for example, mucous and other fluids that may accumulate in the lungs. The trap 702 may comprise any suitable shape and may be formed from any suitable metallic or non-metallic materials. Preferably, the trap 702 should be formed from a lightweight, non-corrosive material. In addition, the trap 702 should be designed in such a manner as to allow for effective and efficient cleaning. In one exemplary embodiment, the trap 702 may comprise disposable liners that may be removed when the trap 702 is full. The trap 702 may be formed from a transparent material or comprise an indicator window so that it may be easily determined when the trap 702 should be emptied or cleaned. A lightweight trap 702 increases the patient's mobility.

The filter/one-way valve 706 may be attached to the trap 702 by any suitable means, including threaded fittings or compression type fittings commonly utilized in compressor connections. The filter/one-way valve 706 serves a number of functions. The filter/one-way valve 706 allows the air from the individual's lung or lungs 708 to exit the trap 702 while maintaining the fluid discharge and solid particulate matter in the trap 702. This filter/one-way valve 706 would essentially maintain the pressure in the trap 702 below that of the pressure inside the individual's lung or lungs 708 so that the flow of air from the lungs 708 to the trap 702 is maintained in this one direction. The filter portion of the filter/one-way valve 706 may be designed to capture particulate matter of a particular size, which is suspended in the air, but allows the clean air to pass therethrough and be vented to the ambient environment. The filter portion may also be designed in such a manner as to reduce the moisture content of the exhaled air.

The air carrying conduit 704 connects the trap 702 to the lung or lungs 708 of the patient through the filter/one-way valve 706. The air carrying conduit 704 may comprise any suitable biocompatible tubing having a resistance to the gases contained in air. The air carrying conduit 704 comprises tubing having an inside diameter in the range from about 1/16 inch to about 1/2 inch, and more preferably from about 1/8 inch to about 1/4 inch. The filter/one-way valve 706 may comprise any suitable valve, which allows air to flow from the lung or lungs 708 through the air carrying conduit 704, but not from the trap 702 back to the lungs 708. For example, a simple check valve may be utilized. The air carrying conduit 704 may be connected to the filter/one-way valve 706 by any suitable means. Preferably, a quick release mechanism is utilized so that the trap may be easily removed for maintenance.

As illustrated in FIG. 7, the air carrying conduit 704 passes through the lung 708 at the site determined to have the highest degree of collateral ventilation. If more than one site is determined, multiple air carrying conduits 704 may be utilized. The connection of multiple air carrying conduits 704 to the filter/one-way valve 706 may be accomplished by any suitable means, including an octopus device similar to that utilized in scuba diving regulators.

The air carrying conduit 704 is preferably able to withstand and resist collapsing once in place. Since air will travel through the conduit 704, if the conduit is crushed and unable to recover, the effectiveness of the system is diminished. Accordingly, a crush recoverable material may be incorporated into the air carrying conduit 704 in order to make it crush recoverable. Any number of suitable materials may be utilized. For example, nitinol incorporated into the conduit 704 will give the conduit collapse resistance and collapse recovery properties.

Expandable features at the end of the conduit 704 may be used to aid in maintaining contact and sealing the conduit 704 to the lung pleura. Nitinol incorporated into the conduit 704 will provide the ability to deliver the conduit 704 in a compressed state and then deployed in an expanded state to secure it in place. Shoulders at the end of the conduit 704 may also provide a mechanical stop for insertion and an area for an adhesive/sealant to join as described in detail subsequently.

In order for the exemplary collateral ventilation bypass trap system 700 to function, an airtight seal is preferably maintained where the air carrying conduit 704 passes through the thoracic cavity and lungs 708. This seal is maintained in order to sustain the inflation/functionality of the lungs. If the seal is breached, air can enter the cavity and cause the lungs to collapse. One exemplary method for creating the seal comprises forming adhesions between the visceral pleura of the lung and the inner wall of the thoracic cavity. This may be achieved using either chemical methods, including irritants such as doxycycline and/or bleomycin, surgical methods, including pleurectomy or thorascopic talc pleurodesis, or radiotherapy methods, including radioactive gold or external radiation. All of these methods are known in the relevant art for creating pleurodesis. In another alternate exemplary embodiment, a sealed joint between the air carrying conduit 704 and the outer pleural layer includes using various glues to help with the adhesion/sealing of the air carrying conduit 704. Currently, Focal Inc. markets a sealant available under the tradename FOCALSEAL®-L surgical sealant which is indicated for use on a lung for sealing purposes. FOCALSEAL®-L (PEG-lactide-glycolide-acrylate) surgical sealant is activated by light in order to cure the sealant. Another seal available under the tradename THOREX™ (cross-linked bovine serum albumin) surgical sealant, which is manufactured by Surgical Sealants Inc., is currently conducting a clinical trial for lung sealing indications. THOREX™ surgical sealant is a two-part sealant that has a set curing time after the two parts are mixed.

The creation of the opening in the chest cavity may be accomplished in a number of ways. For example, the procedure may be accomplished using an open chest procedure, aternotomy or thoracotomy. Alternately, the procedure may be accomplished using a laproscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

The air carrying conduit 704 may be sealed to the skin at the site by any of the means and methods described above with respect to the oxygen carrying conduit 704 and illustrated in FIGS. 2 through 5.

In operation, when an individual exhales, the pressure in the lungs is greater than the pressure in the trap 702. Accordingly, the air in the highly collateralized areas of the lung will travel through the air carrying conduit 704 to the trap 702. This operation will allow the individual to more easily and completely exhale.

Figure 8:
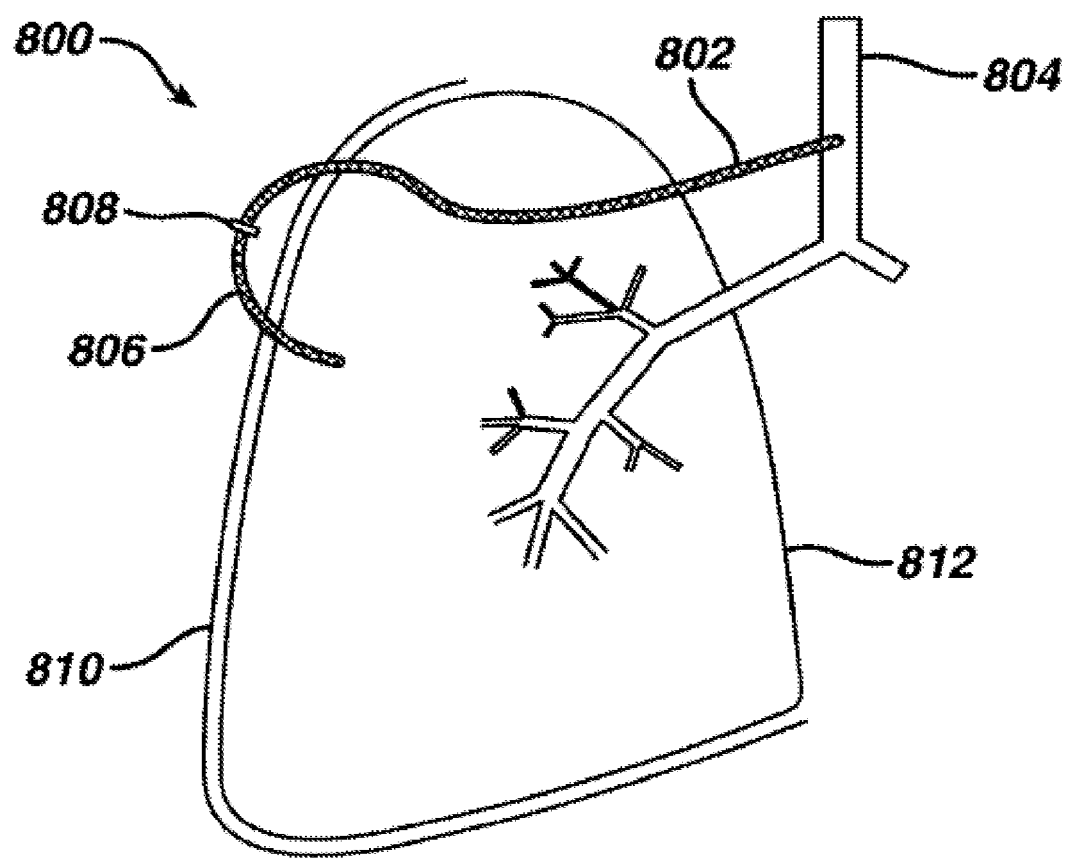
FIG. 8 is a diagrammatic representation of a second exemplary embodiment of a collateral ventilation bypass system in accordance with the present invention.

FIG. 8 illustrates another exemplary collateral ventilation bypass system 800. In this exemplary embodiment, the trachea is utilized to remove trapped air rather than the native airways. As illustrated, a first conduit 802 extends from the patient's trachea 804, or other proximal airways, including the bronchus, to a position external of the patient's body. A second conduit 806 is connected to the first conduit 802 via a fitting 808 and passes through the thoracic wall 810 and passes through the lung 812 at the site determined to have the highest degree of collateral ventilation. If more than one site is determined to have a high degree of collateral ventilation, multiple conduits may be utilized. In operation, when the patient exhales, the pressure in the lungs is greater than the pressure in the trachea 804; accordingly, the air in the highly collateralized areas of the lung will travel through the first and second conduits 802, 806 to the trachea 804 and out of the patient's nose and mouth with the normally exhaled air.

The first and second conduits 802, 806 may comprise any suitable biocompatible tubing having a resistance to the various gases and other constituents contained in inhaled and exhaled air. As in previously described embodiments, the first and second conduits 802, 806 comprise tubing having an inside diameter in the range from about 1/16 inch to about 1/2 inch, and more preferably from about 1/8 inch to about 1/4 inch.

The connection of the first conduit 802 to the trachea 804 may comprise any suitable airtight seal. For example, a fluid communication between the trachea 804 and the first conduit 802 may be established in a manner identical to that established for a tracheotomy. In addition, as stated above, in order for the collateral ventilation bypass system 800 to function, an airtight seal is preferably maintained where the second conduit 806 passes through the thoracic wall 810 and into the lungs 812. An exemplary method for creating this airtight seal comprises forming adhesions between the visceral pleura of the lung and the parietal pleura. This may be achieved using either chemical methods, including irritants, surgical methods, including pleurectomy or thorascopic talc pleurodesis, or radiotherapy methods, including radioactive gold or external radiation.

The creation of the opening in the thoracic wall may be accomplished in a number of ways. For example, the procedure may be accomplished using an open chest procedure, aternotomy or thoracotomy. Alternately, the procedure may be accomplished using a laproscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

The conduits 802, 806 may be sealed to the skin at the sites by any known methods, including those described above with respect to FIGS. 2 through 5. The connection of the extrathoracic component, conduit 806, may comprise a drug, chemical, agent, or other means for preventing or substantially reducing the risk of infection.

The fitting 808 connecting the first and second conduits 802, 806 may comprise any suitable device for creating an airtight seal. The fitting 808 may comprise any type of threaded or non-threaded union, compression fittings similar to compressor type fittings or any other suitable device for establishing an airtight seal and providing for quick release between the two ends of the fitting 808. This type of design would allow easy access for periodic maintenance of the system 800, for example, cleaning the conduits 802, 806. Since the fitting 808 is external to the body, access to the inner body component of the system 800 would be easier. Essentially, access of the system 800 from outside the body would allow for maintenance and diagnosis/observation of the system 800 without subjecting the patient to additional stress and risk. It would also be less time consuming for the doctor.

Figure 9:
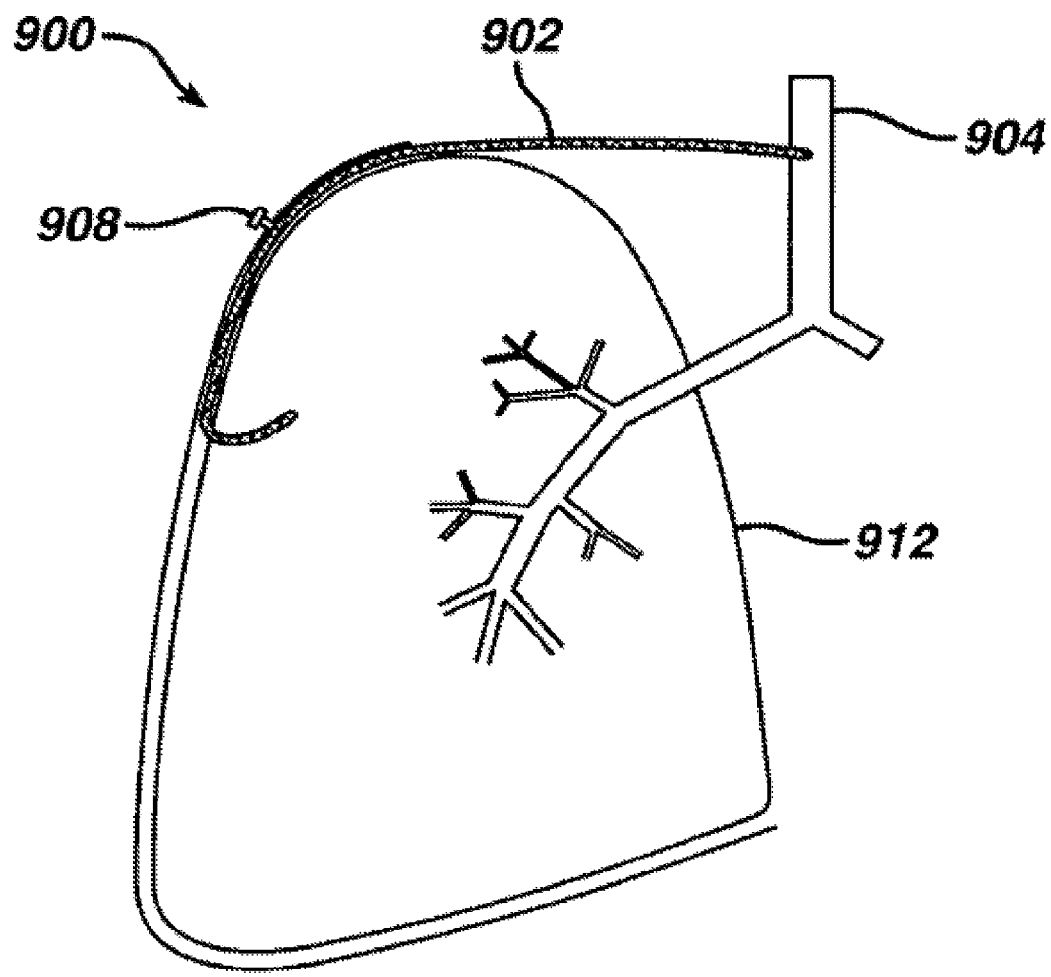
FIG. 9 is a diagrammatic representation of a third exemplary embodiment of a collateral ventilation bypass system in accordance with the present invention.

FIG. 9 illustrates an alternate exemplary embodiment of the exemplary collateral ventilation bypass system 800 described above. In this exemplary embodiment, the system 900 comprises an externally positioned access port 908. As illustrated, a conduit 902 extends from the patient's trachea 904, or other proximal airways, including the bronchus, through a suitable passageway internal to the patient's body and then passes through the lung 912 at the site determined to have the highest degree of collateral ventilation. As set forth above, if more than one site is determined to have a high degree of collateral ventilation, multiple conduits may be utilized. At the desired location within the body, the access port 908 may be placed in-line with the conduit 902 such that at least a portion of the access port 908 is accessible outside of the body. Essentially, the access port 908 should allow the patient or a doctor to open the port and access the system 900 within the patient's body for maintenance and diagnosis/observation of the system 900 as described above.

The access port 908 may comprise any suitable device for providing an airtight seal when closed and easy access to the conduit 902 when open. The access port 908 may comprise various valve arrangements and connectors for connecting other components, which may be utilized for various functions. For example, oxygen may be supplied directly to the patient's lungs 912 if needed. In this instance, a valve may be needed to prevent the oxygen from bypassing the lungs 912 and go straight to the trachea 904.

All the remaining components may be the same as described above. In addition, all seals may be accomplished as described above.

Figure 10:
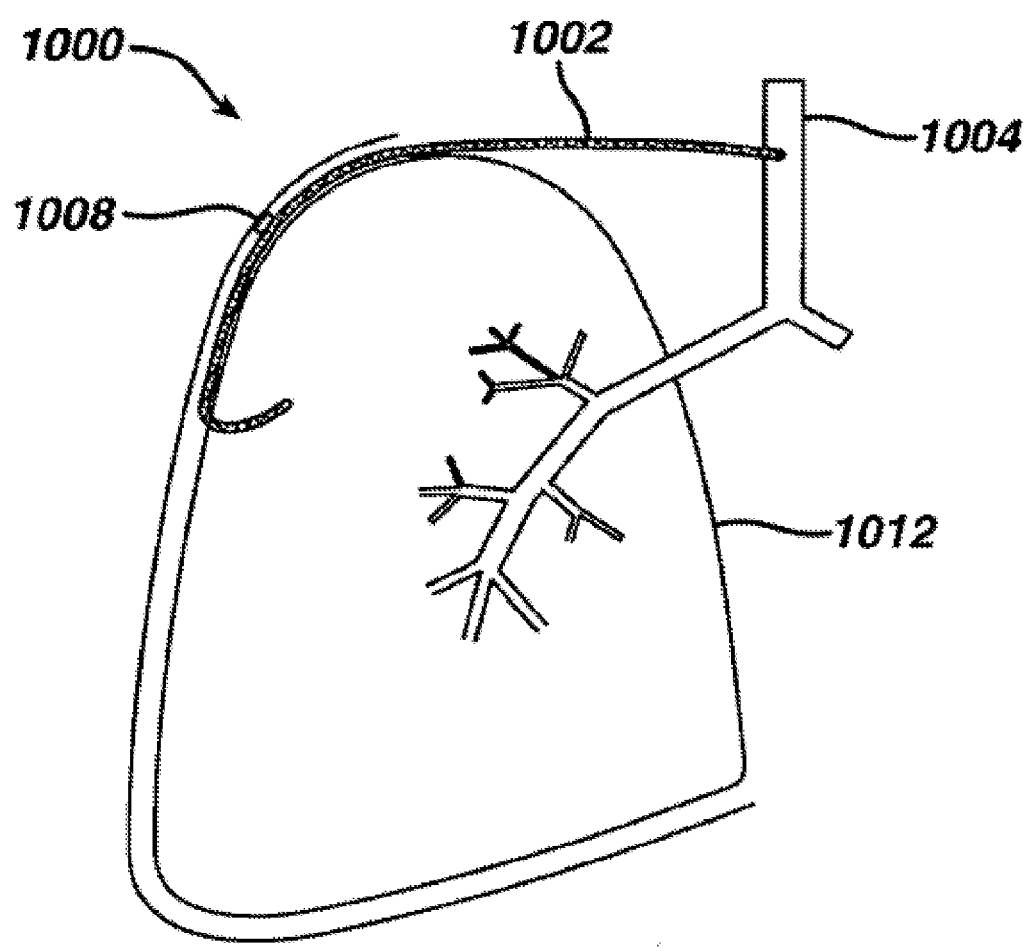
FIG. 10 is a diagrammatic representation of a fourth exemplary embodiment of a collateral ventilation bypass system in accordance with the present invention.

In yet another alternate exemplary embodiment, the extrathoracic access port 908, illustrated in FIG. 9, may be positioned just under the skin so that it is accessible percutaneously. Essentially, the access port would not truly be extrathoracic, but rather just located under the skin and accessible extrathoracically. In this exemplary embodiment access would not be as easily accessible; however, the access point would remain more discrete than the previously described exemplary embodiments. FIG. 10 illustrates this exemplary embodiment.

As illustrated in FIG. 10, the collateral ventilation bypass system 1000 comprises a conduit 1002 that extends from the patient's trachea 1004, or other proximal airways, including the bronchus, through a suitable passageway internal to the patient's body and then passes through the lung 1012 at the site determined to have the highest degree of collateral ventilation. As set forth above, if more than one site is determined to have a high degree of collateral ventilation, multiple conduits may be utilized. At the desired location within the body, an internal access port 1008 may be placed in-line with the conduit 1002. The access port 1008 may comprise any suitable device that allows access via percutaneous means. All remaining components may be the same as described above. In addition, all seals may be accomplished as described above.

It is important to note that in each of the above-described exemplary embodiments, additional components may be added that function to prevent flow from the trachea end of the conduit to the lung. For example, one or more valves may be incorporated throughout the systems to prevent mucus and other substances from entering or re-entering the lung. The main function of the system is to allow exhalation. In theory, patients with emphysema have increased resistance to expiration and not inhalation. Any suitable valves may be utilized, for example, one-way check valves.

Figure 11:
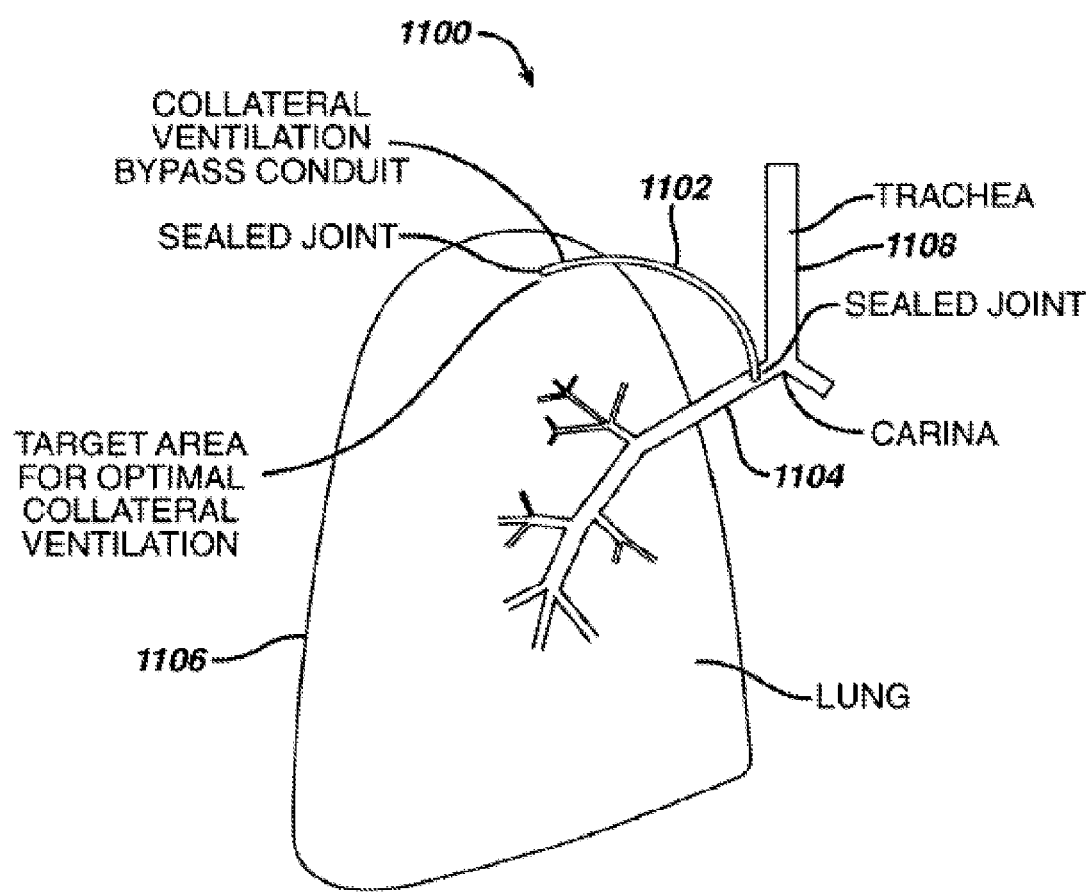
FIG. 11 is a diagrammatic representation of an exemplary embodiment of an intra-thoracic collateral ventilation bypass system in accordance with the present invention.

FIG. 11 illustrates yet another alternate exemplary collateral ventilation bypass system 1100. In this exemplary embodiment, like the exemplary embodiments illustrated in FIGS. 8-10, the trachea or other proximal airways, including the bronchus, is utilized to remove air trapped in the lung or lungs. As illustrated, a conduit 1102 extends from the patient's bronchus 1104 and passes directly into the lung 1106 at the site determined to have the highest degree of collateral ventilation. If more than one site is determined to have a high degree of collateral ventilation, multiple conduits may be utilized. In operation, when the patient exhales, the pressure in the lungs is greater than the pressure in the bronchus 1104; accordingly, the air in the highly collateralized area or areas of the lung will travel through the conduit 1102 to the bronchus 1104, into the trachea 1108 and out of the patient's nose and mouth, not shown, with the normally exhaled air.

The conduit 1102 in this exemplary embodiment does not leave the patient's body. The conduit 1102 may comprise any suitable biocompatible tubing having a resistance to the various gases and other constituents contained in inhaled and exhaled air. As in previously described exemplary embodiments, the conduit 1102 comprises tubing having an inside diameter in the range from about 1/16 inch to about 1/2 inch, and more preferably in the range from about 1/8 inch to about 1/4 inch.

The conduit 1102 preferably is able to withstand and resist collapsing. Since air will travel through the conduit 1102, if the conduit 1102 is crushed and is unable to recover, the effectiveness of the procedure may be substantially reduced. Therefore, various materials may be incorporated into the conduit 1102 to make it crush recoverable. For example, materials exhibiting super elastic or shape memory properties or characteristics may be utilized. Nitinol incorporated into the conduit 1102 will give the component collapse resistance and collapse recovery properties. The conduit 1102 may comprise a polymeric coating over a suitably arranged nitinol base structure. The polymeric coating or cover layer may be formed from any suitable polymeric materials, including polytetrafluoroethylene, silicone and polyurethanes.

The conduit 1102 may also comprise modified ends. For example, expandable features at each end may be utilized to maintain contact and sealing between the conduit 1102 and/or the bronchus 1104, the trachea 1108, and the lung 1106 pleura. Once again, nitinol or other similar property materials may be incorporated into the conduit 1102 and thus provide the conduit 1102 to be delivered in a smaller diameter compressed state and then deployed in a larger diameter expanded state to help secure it in place. Alternately, shoulders at each end of the conduit 1102 may also provide a mechanical stop for insertion and an area for an adhesive/sealant to join.

The conduit 1102 may be introduced into the body of the patient in a number of ways. In one exemplary embodiment, the conduit 1102 may be introduced utilizing an open-chest procedure, for example, a sternotomy or thoracotomy. In al alternate exemplary embodiment, the conduit 1102 may be introduced utilizing a laproscopic technique to make the procedure less invasive. It is important to note that the conduit 1102 may be incorporated into the opening creating device. If the conduit 1102 is incorporated with the opening creating device, the conduit 1102 may be inserted and established in the same step as the opening creation.

As stated in the above-described exemplary embodiments, in order for the collateral ventilation bypass system 1100 to function, an airtight seal is preferably made between the conduit 1102 and the outer pleural layer of the lung 1106. This seal is maintained in order to sustain the inflation/functionality of the lungs. If the seal is breached, air can enter the pleural space and cause the lungs to collapse. One method for creating the seal involves pleuroderis or forming adhesions between the visceral pleura of the lung and the inner wall of the thoracic cavity as briefly described above and in more detail subsequently. In another alternate exemplary embodiment, a sealed joint between the conduit 1102 and the outer pleural layer includes using various glues to help with the adhesion/sealing of the conduit 1102 as described above. Regardless of the procedure utilized, the seal should be established while the lung is at least partially inflated in order to maintain a solid adhesive surface. The opening may then be made after the joint has been adequately created between the conduit 1102 and the lung pleural surface. The opening should be adequate in cross-sectional area in order to provide sufficient decompression of the hyperinflated lung.

The connection of the conduit 1102 to the trachea or bronchus 1104 should also be an airtight seal. For example, fluid communication between the bronchus 1104 and the conduit 1102 may be established in a manner identical to that established for a tracheotomy.

The conduit 1102 may be positioned at any suitable location within the patient's body. Preferably, the conduit 1102 is positioned such that it will not affect the patient's ability to function normally.

It is important to note that in the above-described exemplary embodiment, additional components may be added that function to prevent flow from the bronchus to the lung. For example, one or more valves or filters may be incorporated into the conduit to prevent mucus and other substances from entering or re-entering the lung. The main function of the collateral ventilation bypass system is to allow exhalation. In theory, patients with emphysema have increased resistance to expiration and not inspiration. Any suitable valves may be utilized, for example, one-way check valves.

As described above, pulmonary emphysema leads to the breakdown of lung tissue, which in turn leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung or lungs to establish in a hyperinflated state where an individual can only take short shallow breaths. Essentially, air is not effectively expelled and stale air accumulates in the lungs. Once the stale air accumulates in the lungs, the individual is deprived of oxygen.

Lung volume reduction surgery is an extremely traumatic procedure that involves removing part or parts of the lung or lungs. By removing the portion of the lung or lungs which is hyperinflated, pulmonary function may improve due to a number of mechanisms, including enhanced elastic recoil, correction of ventilation/perfusion mismatch and improved efficiency of respiratory work. Essentially, as the emphysematous tissue volume is reduced, the healthier tissue is better ventilated. However, lung volume reduction surgery possesses a number of potential risks as described in more detail subsequently.

The collateral ventilation bypass trap system 700, illustrated in FIG. 7, and the collateral ventilation bypass system 800, illustrated in FIG. 8, utilize the collateral ventilation phenomenon to allow the air entrapped in the lung or lungs to bypass the native airways and be expelled either to a containment vessel or to the ambient environment. However, in an alternate exemplary embodiment, a device, which works similarly to collateral ventilation bypass and provides results commensurate with lung volume reduction surgery, is disclosed herein. Essentially, in this exemplary embodiment, the invention is directed to a device and associated method for assisting pulmonary decompression. In other words, the present invention is directed to pulmonary decompression assist device and method that would provide a means for the removal of trapped air in the emphysematous lung and the maintenance of the emphysematous area compressed to a smaller volume, with the result being that healthier lung tissue will have more volume in the thoracic cavity to ventilate. The effects of this device may be similar to that of lung volume reduction surgery.

The exemplary pulmonary decompression assist device of the present invention may be strategically positioned in the body of a patient such that it is in fluid communication with the patient's lung or lungs and the external environment. The device would allow air to be exhaled out from the lung or lungs through the native airways while assisting in removing trapped air in the hyperinflated portion of the lung or lungs. Lung volume reduction surgery is an extremely invasive and traumatic procedure that in a substantially high number of cases causes the patients undergoing the procedure to become excluded from being a candidate for lung transplantation. The device of the present invention provides for a minimally invasive procedure for causing the lung volume to reduce similarly to lung volume reduction surgery while allowing the patient to remain a viable candidate for lung transplantation.

The exemplary pulmonary decompression device may utilize any number of known techniques for creating a sufficient pressure differential between the inside of the lung or lungs and an area external of the lung or lungs to allow the trapped air to exit the lung or lungs. The device may comprise any suitable device such as pumps or fans or any other means to create the pressure differential. If the collateral airflow and areas of emphysema are situated so that air may reinflate that area, the device may be configured to continuously draw air from the lung or lungs to maintain a smaller lung volume of the emphysematous tissue. The device may be left in the patient's body indefinitely in order to maintain the compression of the emphysematous tissue in the lung or lungs. In addition, in order to maintain the cleanliness of the device and the safety of the patient, the device may be constructed as a disposable device and be replaced at various intervals. In addition, portions of the device that are easily accessible may be made disposable. Alternately, the device may be constructed for easy removal, easy cleaning and easy replacement.

Figure 12:
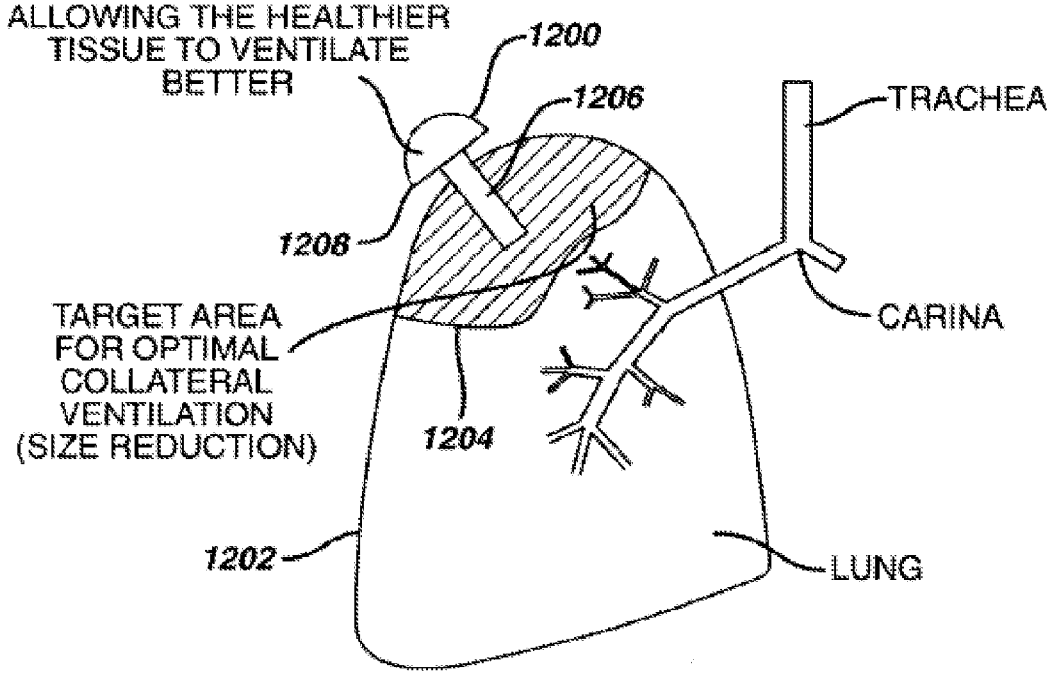
FIG. 12 is a diagrammatic representation of an exemplary pulmonary decompression device in accordance with the present invention.

Referring to FIG. 12, there is illustrated an exemplary pulmonary decompression device 1200 in accordance with the present invention. As described herein, there is generally an optimal location to penetrate the outer pleura of the lung to access the most collaterally ventilated area or areas of the lung and a variety of techniques to locate the area or areas. Once the desired location is determined, the decompression device 1200 may be inserted into the lung 1202. On insertion and placement of the decompression device 1200 into the lung 1202, it is particularly advantageous to establish an airtight seal of the parietal and visceral pleurae. If a proper airtight seal is not created between the decompression device, parietal and visceral pleurae, then a pneumothorax may occur.

It is important to note that one or more devices may be utilized in each lung to remove trapped air from highly collateralized areas. Alternately, a single device with multiple conduits may be utilized. As illustrated in FIG. 12, the decompression device 1200 is placed in the lung 1202 in the area of highest collateral ventilation 1204. In one exemplary embodiment, only a first section 1206 of the decompression device 1200 is positioned within the lung 1202 while a second section 1208 of the decompression device 1200 is secured external to the lung 1202. The sealing of the device 1200 may be made in accordance with any of the devices and methodologies described herein.

At least a portion of the second section 1208 is external to the patient's body. The portion of the second section 1208 that is external to the patient's body may exit the body at any suitable location. In one exemplary embodiment, the portion of the second section 1208 exists the body through the chest and thus may be sealed in accordance with any of the devices and methodologies described herein.

The first section 1206 may comprise any suitable biocompatible material configured to facilitate the flow of air from the lung 1202. For example, the first section 1206 may comprise a conduit similar in size, material and construction as the other conduits described herein. The second section 1208 may be connected to the first section 1206 by any suitable means, including threaded unions or compression type fittings. The second section 1208 comprises a housing for an apparatus that draws air from the hyperinflated portion of the lung 1204 through the first section 1206 and directs it out of the patient's body. The apparatus may include any suitable device for creating a pressure differential between the inside and outside of the lung 1202 such that air will easily flow from the lung 1202. The apparatus may include a miniature pump or fan. The miniature pump or fan may be powered by any suitable means, including batteries or rechargeable batteries. In the above-described exemplary embodiment, the miniature pump or fan and its power supply may be housed completely in the housing. In other alternate exemplary embodiments, one or more of the pump/fan or power supply may be located remotely from the second section 1208. For example, the second section 1208 may simply comprise a second conduit removably connected on one end to the first conduit and on a second end to the apparatus that draws air from the diseased section of the lung 1204.

In the exemplary embodiment illustrated in FIG. 12, the apparatus that draws air from the diseased section of the lung 1204 and its associated power supply are housed within the second section 1208. This design provides the most freedom for the patient. Various known miniature vacuum pumps or fans may be used to continuously draw air from the diseased section of the lung 1204, thereby reducing the emphysematous tissue volume and allowing the healthier tissue to ventilate better. The miniature fan/pump and associated power supply may be separate components or a single component. These miniature devices may comprise microelectromechanical systems or MEMS, or any other suitable device for drawing air from one location and venting it to a second location. The decompression device 1200 should be designed to be easily maintained. For example, the second section 1208 may be made such that it can be removed, the power supply recharged and the other components cleaned and then replaced. Alternately, the second section 1208 may simply be disposable.

The power supply may comprise any suitable means for supplying power continuously for extended periods of time. The power supply may comprise batteries, rechargeable batteries, piezoelectric devices that generate electrical power from mechanical strain or any other suitable device. In addition, other than a fan or pump for creating a vacuum, some type of switching elements may be utilized for creating a slight pressure differential.

Figure 13A:
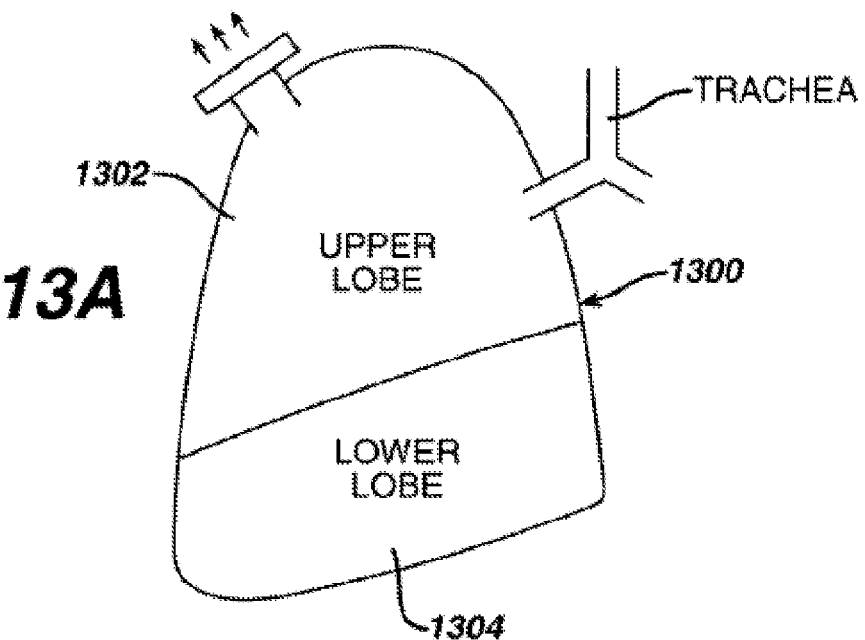
FIGS. 13a and 13b are diagrammatic representations of the effects on lung volume in accordance with the present invention.
Figure 13B:
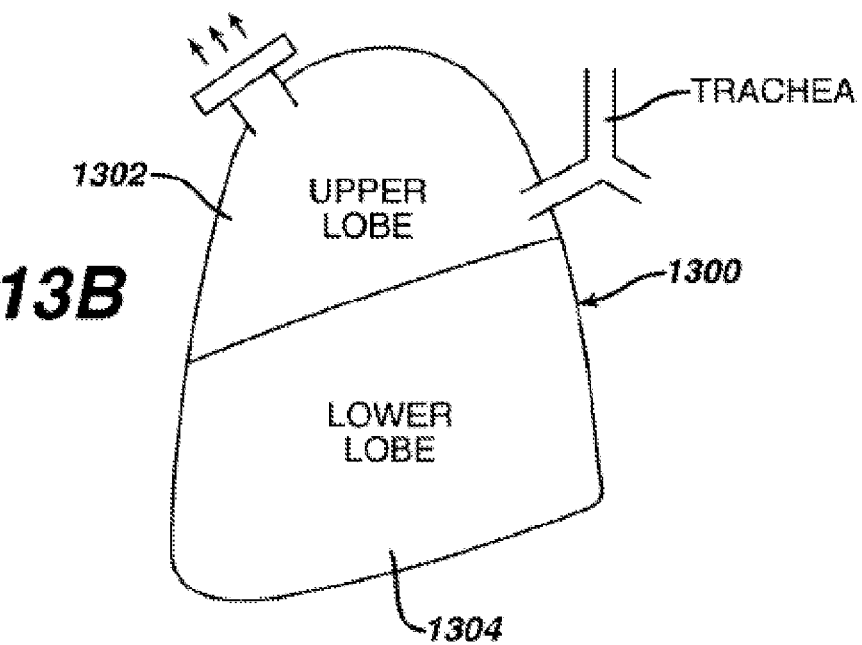

Accordingly, rather than a resection of the lung tissue, the decompression device removes trapped air from the emphysematous section of the lung and maintains the emphysematous section in a compressed state or smaller volume, thereby allowing the healthier lung tissue more volume in the thoracic cavity to ventilate. FIG. 13a illustrates the decompression device 1200 removing air from the hyperinflated portion 1302 of the lung 1300. As illustrated, in this lung, the hyperinflated or emphysematous portion 1302 of the lung 1300 is larger than the healthy section or portion 1304 of the lung 1300. As the device 1300 continues to remove the accumulated or trapped air, the volume of the hyperinflated portion 1302 of the lung 1300 shrinks, thereby allowing the healthier portion 1304 more room to fully ventilate, thereby increasing in volume as illustrated in FIG. 13b.

In an alternate exemplary embodiment, a more passive device may be utilized for reducing the size of the lung. A lung reduction device may be strategically positioned about the body of a patient and access the patient's lung or lungs. The device would allow air to be expelled from the lung or lungs while preventing air from re-entering therethrough. Essentially, the device would comprise at least one component that accesses the outer pleural layer of the emphysematous portion or portions of the patient's lung or lungs. This at least one component will utilize the collateral ventilation of the lung or lungs and allow the entrapped air in the emphysematous portion or portions of the lung or lungs to bypass the native airways and expel through to the outside of the body through a second component. The second component includes a feature that allows air to flow from the lung or lungs to the ambient environment, but not from the ambient environment back into the lung or lungs. If the collateral airflow and areas of emphysema are situated so that air cannot reinflate these portions of the lung or lungs, then a size reduction of that area of the lung should occur.

Figure 14A:
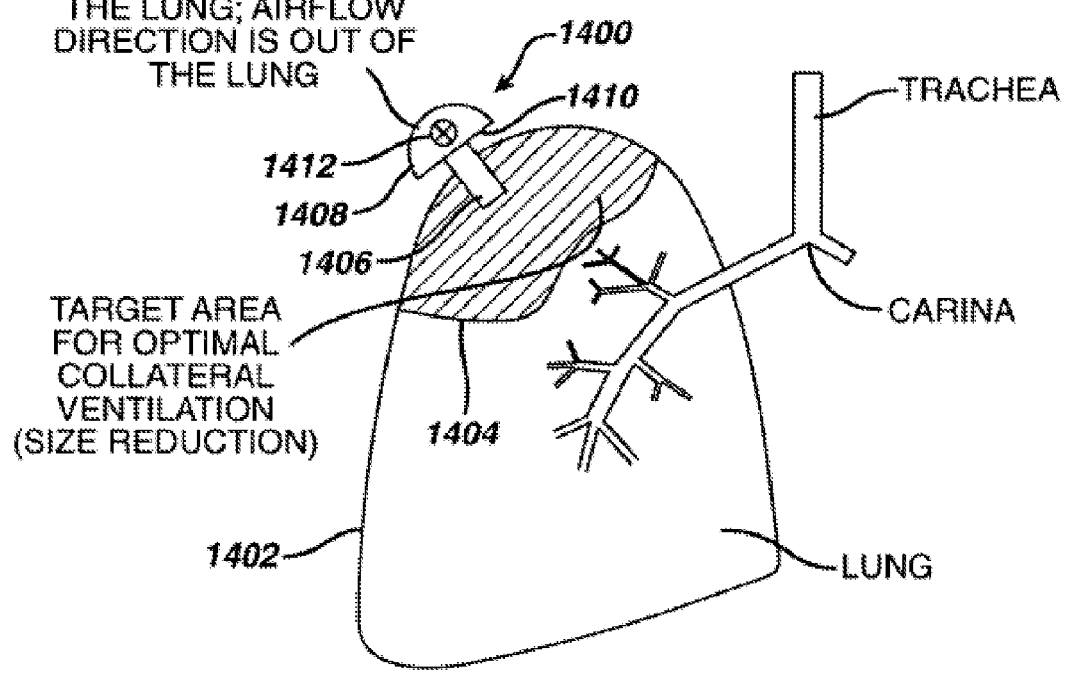
FIGS. 14a and 14b are diagrammatic representations of the effects on lung volume reduction utilizing the lung reduction system in accordance with the present invention.
Figure 14B:
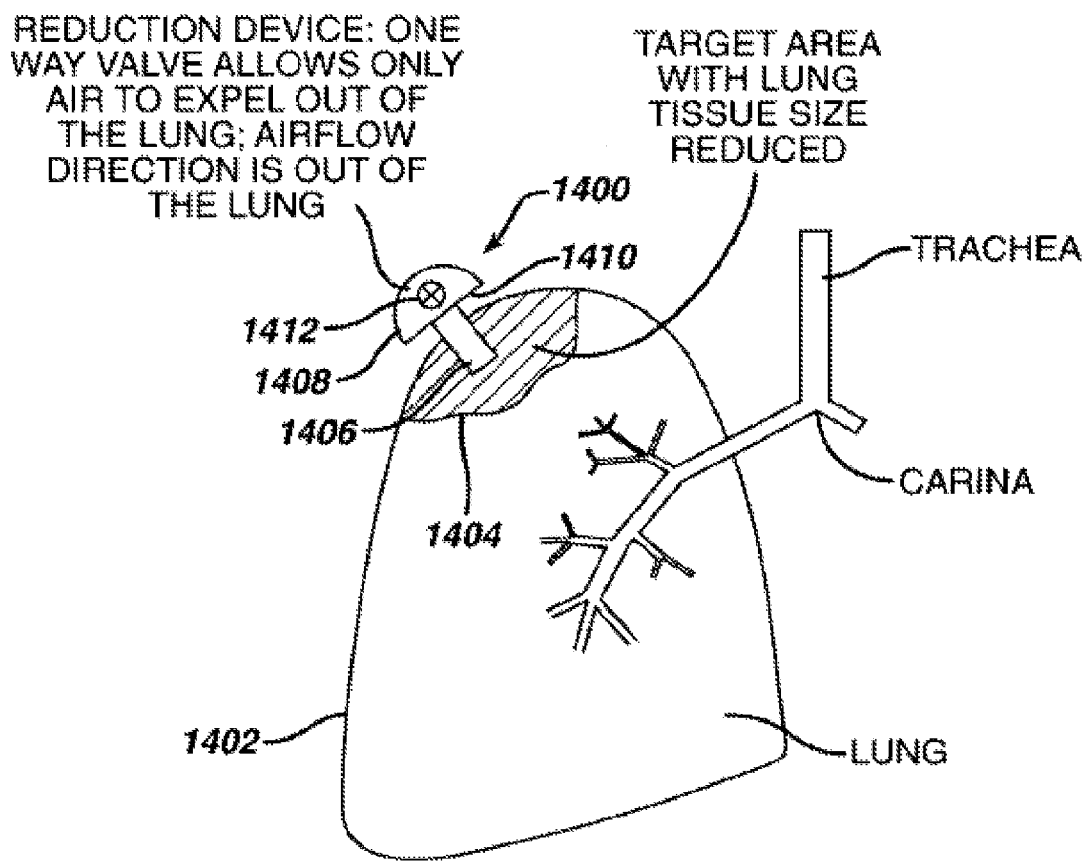

Referring to FIGS. 14a and 14b, there is illustrated an exemplary lung reduction device 1400 in accordance with the present invention. As described herein, there is generally an optimal location to penetrate the outer pleura of the lung to access the most collaterally ventilated area or areas of the lung or lungs and a variety of techniques to locate these areas. Once the desired location or locations are determined, the lung reduction device 1400 may be inserted into the lung 1402. The insertion or introduction of the device 1400 may be accomplished utilizing a number of minimally invasive techniques, for example, percutaneously or endoscopically, thereby substantially reducing the risk to the patient and trauma to the lung or lungs. It is important to note that all of the systems and devices described herein are preferably implanted utilizing minimally invasive techniques. On insertion and placement of the lung reduction device 1400 into the lung 1402, it is particularly advantageous to establish an airtight seal of the parietal and visceral pleurae utilizing any of the techniques, devices and processes described herein. If an airtight seal is not established between the lung reduction device 1400, parietal and visceral pleurae, then a pneumothorax may occur.

It is important to note that one or more lung reduction devices may be utilized in each lung to remove trapped air from highly collateralized areas. Alternately, a single lung reduction device in fluid communication, through conduits or other similar means, with multiple locations may be utilized. For case of explanation, a single device and single diseased portion is described and illustrated. Once again, referring to FIGS. 14a and 14b, the lung reduction device 1400 is implanted in the lung 1402 in the area of highest collateral ventilation 1404. In the exemplary embodiment illustrated, a first section 1406 of the lung reduction device 1400 is positioned within the inner volume of the lung 1402 while a second section 1408 of the lung reduction device 1400 is secured to the patient's body external to the lung 1402. The first section 1406 of the device 1400 accesses the parenchyma of the lung 1402. The parenchyma are the cells in tissues that are concerned with function rather than structure. In other words, the first section 1406 accesses the alveoli of the lung 1402. The attainment of an airtight seal of the lung reduction device 1400 may be made in accordance with any of the devices and methodologies described herein.

At least a portion of the second section 1408 is external to the patient's body. The portion of the second section 1408 that is external to the patient's body may exit or extend from the body at any suitable location. Preferably, the portion of the second section 1408 exits at a location that proves to be of minimum burden to the patient and allows for easy access for maintenance, repair or replacement. In one exemplary embodiment, the portion of the second section 1408 exits the body through the chest and thus may be sealed in accordance with any of the devices and methodologies described herein.

The first section 1406 may comprise any suitable device for facilitating the flow of air from the lung 1402. For example, the first section 1406 may comprise a conduit similar in size, material and construction or any of the other conduits described herein. The second section 1408 may be connected to the first section 1406 by any suitable means, including threaded connectors, unions or compression type fittings.

The second section 1408 may comprise any suitable means for allowing one-way airflow. In one exemplary embodiment, the second section 1408 comprises a housing 1410 and a one-way valve 1412. The housing 1410 may be formed from any suitable biocompatible material. A portion of the housing 1410 houses the one-way valve 1412 while another portion of the housing 1410 forms the portion that is external to the body. The one-way valve 1412 may comprise any suitable pressure actuated valve, which allows air to flow from one lung 1402 to the ambient environment. The one-way valve 1412 may comprise a check valve, a reed valve, needle valves, flapper check valves or any other suitable device. In preferred embodiments, the one-way valve 1412 requires only a slight pressure differential to open and allow air flow from the lung 1402 to the ambient or external environment, but does not allow air flow back into the lung 1402 even under substantial reverse pressure.

In operation, when the person inhales, the volume of the thoracic cavity increases by the contraction of the diaphragm and thus the volume of the lungs also increases. As the volume of the lungs increase, the pressure of the air in the lungs falls slightly below the pressure of the air external to the body and thus air flows through the respiratory passageways into the lungs until the pressure equalizes. When the person exhales, the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. However, in the diseased area 1404 of the lung 1402, normal exhalation does not work for the reasons described herein and thus the increased pressure in the lung 1402 opens the one-way valve 1412 and air flows from the diseased portion 1404 through the first section 1406, through the one-way valve 1412 and out of the body.

The lung reduction device 1400 may be left in the lung indefinitely to maintain the compression of the emphysematous tissue lung 1400 as described above with respect to the decompression device. In order to maintain cleanliness and safety, the lung reduction device 1400 or at least portions thereof may be made disposable and thus be replaced at regular intervals or when needed. As the lung reduction device 1400 continues to allow the trapped air to exit the lung 1402, the volume of the hyperinflated or diseased portion 1404 of the lung 1400 shrinks, thereby allowing the healthier portion of the lung 1400 more room to fully ventilate, thereby increasing in volume as illustrated in FIG. 14b.

The lung reduction device 1400 may be left in the body until the area of the compressed emphysematous tissue has permanently compressed, atelectasis. At this point, the lung reduction device 1400 may potentially be removed safely. If healing of the insertion site of the reduction device 1400 has occurred, the fistula created may be permanently sealed.

In the above-described exemplary apparatus and procedure for increasing expiratory flow from a diseased lung using the phenomenon of collateral ventilation, there will be an optimal location to penetrate the outer pleura of the lung to access the most collaterally ventilated area or areas of the lung. In addition, in the above-described exemplary pulmonary decompression assist device, there is an optimal location for decompressing the hyperinflated lung or lungs. As described above, there are a variety of techniques to locate the most collaterally ventilated area or areas of the lungs. Since a device or component of the apparatus functions to allow the air entrapped in the lung to bypass the native airways and be expelled outside of the body, it is particularly advantageous to provide an airtight seal of the parietal (thoracic wall) and visceral (lung) pleurae. If a proper airtight seal is not created between the device, parietal and visceral pleurae, then a pneumothorax (collapsed lung) may occur. Essentially, in any circumstance where the lung is punctured and a device inserted, an airtight seal should preferably be maintained.

One way to achieve an airtight seal is through pleurodesis, i.e. an obliteration of the pleural space. There are a number of pleurodesis methods, including chemical, surgical and radiological. In chemical pleurodesis, an agent such as tetracycline, doxycycline, bleomycin or nitrogen mustard may be utilized. In surgical pleurodesis, a pleurectomy or a thorascopic talc procedure may be performed. In radiological procedures, radioactive gold or external radiation may be utilized. In the present invention, chemical pleurodesis is utilized.

Exemplary devices and methods for delivering a chemical (s) or agent(s) in a localized manner for ensuring a proper airtight seal of the above-described apparatus is described below. The chemical(s), agent(s) and/or compound(s) are used to create a pleurodesis between the parietal and visceral pleura so that a component of the apparatus may penetrate through the particular area and not result in a pneumothorax. There are a number of chemical(s), agent(s) and/or compound (s) that may be utilized to create a pleurodesis in the pleural space. The chemical(s), agent(s) and/or compound(s) include talc, tetracycline, doxycycline, bleomycin and minocycline.

In one exemplary embodiment, a modified drug delivery catheter may be utilized to deliver chemical(s), agent(s) and/or compound(s) to a localized area for creating a pleurodesis in that area. In this exemplary embodiment, the pleurodesis is formed and then the conduit 704, as illustrated in FIG. 7, is positioned in the lung 708 through the area of the pleurodesis. The drug delivery catheter provides a minimally invasive means for creating a localized pleurodesis. Referring to FIG. 15, there is illustrated an exemplary embodiment of a drug delivery catheter that may be utilized in accordance with the present invention. Any number of drug delivery catheters may be utilized. In addition, the distal tip of the catheter may comprise any suitable size, shape or configuration thereby enabling the formation of a pleurodesis having any size, shape or configuration.

As illustrated in FIG. 15, the catheter 1500 is inserted into the patient such that the distal end 1502 is positioned in the pleural space 1504 between the thoracic wall 1508 and the lung 1506. In the illustrated exemplary embodiment, the distal end 1502 of the catheter 1500 comprises a substantially circular shape that would allow the chemical(s), agent(s) and/or compound(s) to be released towards the inner diameter of the substantially circular shape as indicated by arrows 1510. The distal end 1502 of the catheter 1500 comprising a plurality of holes or openings 1512 through which the chemical(s), agent(s) and/or compound(s) are released. As stated above, the distal end 1502 may comprise any suitable size, shape or configuration. Once the chemical(s), agent(s) and/or compound(s) are delivered, the catheter 1500 may be removed to allow for implantation of the conduit 704 (FIG. 7). Alternately, the catheter 1500 may be utilized to facilitate delivery of the conduit 704.

The distal end or tip 1502 of the catheter 1500 should preferably maintain its desired size, shape and/or configuration once deployed in the pleural space. This may be accomplished in a number of ways. For example, the material forming the distal end 1502 of the catheter 1500 may be selected such that it has a certain degree of flexibility for insertion of the catheter 800 and a certain degree of shape memory such that it resumes its original or programmed shape once deployed. Any number of biocompatible polymers with these properties may be utilized. In an alternate embodiment, another material may be utilized. For example, a metallic material having shape memory characteristics may be integrated into the distal end 1502 of the catheter 1500. This metallic material may include nitinol or stainless steel. In addition, the metallic material may be radiopaque or comprise radiopaque markers. By having a radiopaque material or radiopaque markers, the catheter 1500 may be viewed under x-ray fluoroscopy and aid in determining when the catheter 1500 is at the location of the highest collateral ventilation.

In another alternate exemplary embodiment, a local drug delivery device may be utilized to deliver the pleurodesis chemical(s), agent(s) and/or compound(s). In this exemplary embodiment, the pleurodesis is formed and then the conduit 704, as illustrated in FIG. 7, is positioned in the lung 708 through the pleurodesis. In this exemplary embodiment, chemical(s), agent(s) and/or compound(s) may be affixed to an implantable medical device. The medical device is then implanted in the pleural cavity at a particular site and the chemical(s), agent(s) and/or compound(s) are released therefrom to form or create the pleurodesis.

Any of the above-described chemical(s), agent(s) and/or compound(s) may be affixed to the medical device. The chemical(s), agent(s) and/or compound(s) may be affixed to the medical device in any suitable manner. For example, the chemical(s), agent(s) and/or compound(s) may be coated on the device utilizing any number of well known techniques including, spin coating, spraying or dipping, they may be incorporated into a polymeric matrix that is affixed to the surface of the medical device, they may be impregnated into the outer surface of the medical device, they may be incorporated into holes or chambers in the medical device, they may be coated onto the surface of the medical device and then coated with a polymeric layer that acts as a diffusion barrier for controlled release of the chemical(s), agent(s) and/or compound(s), they may be incorporated directly into the material forming the medical device, or any combination of the above-described techniques. In another alternate embodiment, the medical device may be formed from a biodegradable material which elutes the chemical(s), agent(s) and/or compound(s) as the device degrades.

The implantable medical device may comprise any suitable size, shape and/or configuration, and may be formed using any suitable biocompatible material. FIG. 16 illustrates one exemplary embodiment of an implantable medical device 1600. In this embodiment, the implantable medical device 1600 comprises a substantially cylindrical disk 1600. The disk 1600 is positioned in the pleural space 1602 between the thoracic wall 1604 and the lung 1606. Once in position, the disk 1600 elutes or otherwise releases the chemical(s), agent(s) and/or compound(s) that form the pleurodesis. The release rate may be precisely controlled by using any of the various techniques described above, for example, a polymeric diffusion barrier. Also, as stated above, the disk 1600 may be formed from a biodegradable material that elutes the chemical(s), agent(s) and/or compound(s) as the disk 1600 itself disintegrates or dissolves. Depending upon the material utilized in the construction of the disk 1600, a non-biodegradable disk 1200 may or may not require removal from the pleural cavity 1602 once the pleurodesis is formed. For example, it may be desirable that the disk 1600 is a permanent implant that becomes integral with the pleurodesis.

As described in the previous exemplary embodiment, the disk 1600 may comprise a radiopaque marker or be formed from a radiopaque material. The radiopaque marker or material allows the disk 1600 to be seen under fluoroscopy and then positioned accurately.

In yet another alternate exemplary embodiment, the fluid characteristics of the chemical(s), agent(s) and/or compound (s) may be altered. For example, the chemical(s), agent(s) and/or compound(s) may be made more viscous. With a more viscous chemical agent and/or compound, there would be less chance of the chemical, agent and/or compound moving from the desired location in the pleural space. The chemical(s), agent(s) and/or compound(s) may also comprise radiopaque constituents. Making the chemical(s), agent(s) and/or compounds radiopaque would allow the confirmation of the location of the chemical(s), agent(s) and/or compound(s) with regard to the optimal location of collateral ventilation.

The chemical(s), agent(s) and/or compound(s) as modified above may be utilized in conjunction with standard chemical pleurodesis devices and processes or in conjunction with the exemplary embodiments set forth above.

Anastomosis is the surgical joining of biological tissues to create a communication pathway between them. The opening created between the lung or lungs and the thoracic wall for placement of conduits or other devices as described in detail above is essentially an anastomosis. The creation of this anastomosis may present certain difficulties, for example, the potential for infection. Accordingly, in addition to creating the pleurodesis, it would be highly desirable to accelerate a fibrotic response in the opening or anastomosis created in the thoracic wall. The fibrosis, which may include epithelial or mucosal regrowth, will protect the anastomosis from infection. Therefore, accelerating and aiding the fibrotic response will benefit the patient by minimizing or substantially reducing the risk of infection at the anastomatic site.

Devices and methods are described herein which may accelerate fibrosis at the location of the anastomosis. In one exemplary embodiment, a component may be positioned at the site of the anastomosis. In this exemplary embodiment, the component acts as a structural framework to accelerate/aid in the fibrotic process. In another exemplary embodiment, a device may be positioned at the site of the anastomosis, which applies a compressive force to the tissue surrounding the anastomatic site. The compression of the tissue functions to accelerate and aid in the healing of the anastomosis. Consequently, a fibrotic response would occur and provide protection against potential infection.

Referring now to FIG. 17, there is illustrated a first exemplary embodiment of a means for accelerating a fibrotic/wound healing response in accordance with the present invention. The anastomosis 1702 is formed utilizing any number of known techniques, thereby creating a passageway between the thoracic wall 1704 and the lung 1706. The pleurodesis is formed in the pleural space 1708 as described in detail above. The passageway or anastomosis 1702, when formed, comprises newly exposed bone and tissue which is prone to infection; accordingly, a fibrosis accelerating component 1710 may be affixed to all or a portion of the tissue surrounding the anastomatic site. As briefly described above, the fibrosis accelerating component 1710 functions as a structural framework to accelerate/aid in the fibrotic process. The fibrosis accelerating component 1710 may comprise any suitable biocompatible material that promotes tissue in-growth. In one exemplary embodiment, the fibrosis accelerating component 1710 comprises a fabric formed from Dacron® polyester. The fabric is porous and would allow healing to occur using the fabric as a foundation.

The fabric fibrosis accelerating component 1710 is preferably in contact with at least a portion, and more preferably, with all of the newly exposed tissue. The fabric fibrosis accelerating component 1710 may be formed into a stand alone component which is configured to make contact with the perimeter of the anastomosis 1702. Alternately, the fabric fibrosis accelerating component 1710 may be attached to the perimeter of the anastomosis 1702. The fabric fibrosis accelerating component 1710 may be attached to the anastomosis 1702 utilizing any number of known techniques, including sutures, staples and adhesives.

The fabric fibrosis accelerating component 1710 accelerates healing and fibrosis by acting as a lattice or framework for tissue in-growth. The more quickly the tissue heals, the less likely the chance for infection. However, the fabric fibrosis accelerating component 1710 may be treated with one or more antibiotics or other agents for preventing or eradicating infection. For example, the fabric fibrosis accelerating component 1710 may be treated with one or more antibiotics or a combination of one or more antibiotics and one or more polymers. The one or more polymers may be used to control the elution rate of the one or more antibiotics. Alternately, the fabric fibrosis accelerating component 1710 may be designed with a cuff or pockets designed to hold the one or more antibiotics. In this exemplary embodiment, the cuffs or pockets control the elution rate of the one or more antibiotics rather than the one or more polymers. In addition, various combinations of these designs may be utilized.

In yet another alternate exemplary embodiment, the fabric fibrosis accelerating component 1710 may comprise or be treated with wound healing drugs, agents and/or compounds. Normal wound healing essentially occurs in three stages or phases, which have a certain degree of overlap. The first phase is cellular migration and inflammation. This phase lasts for several days. The second phase is the proliferation of fibroblasts for two to four weeks with new collagen synthesis. The third phase is remodeling of the scar and typically lasts from one month to a year. This third phase includes collagen cross linking and active collagen turnover.

As stated above, there are certain drugs, agents and/or compounds that may be delivered locally to the anastomatic site, via the fabric fibrosis accelerating component 1710, that promotes wound healing which in turn may eliminate or substantially reduce the incidence of infection. For example, increased collagen production early in wound healing leads to greater would strength. Accordingly, collagen may be combined with the fabric fibrosis accelerating component 1710 to increase would strength and promote platelet aggregation and fibrin formation. In addition, certain growth factors may be combined with the repair system to promote platelet aggregation and fibrin formation as well as to increase would strength.

Platelet-derived Growth Factor induces mitoses and is the major mitogen in serum for growth in connective tissue. Platelet Factor 4 is a platelet released protein that promotes blood clotting by neutralizing heparin. Platelet-derived Growth Factor and Platelet Factor 4 are important in inflammation and repair. They are active for human monocytes, neutrophils, smooth muscle cells, fibroblasts and inflammation cells. Transforming Growth Factor-β is a part of a complex family of polypeptide hormones or biological factors that are produced by the body to control growth, division and maturation of blood cells by the bone marrow. Transforming Growth Factor-β is found in tissues and platelets, and is known to stimulate total protein, collagen and DNA content in wound chambers implanted in vivo. Transforming Growth Factor-β in combination with collagen has been shown to be extremely effective in wound healing.

A series of reactions take place in the body whenever a blood clot begins to form. A major initiator of these reactions is an enzyme system called the Tissue Factor/VIIa complex. Accordingly, Tissue Factor/VIIa may be utilized to promote blood clot formation and thus enhance wound healing. Other agents which are known to initiate thrombus formation include thrombin, fibrin, plasminogin-activator initiator, adenosine diphosphate and collagen.

The use of these drugs, agents and/or compounds in conjunction with the fabric fibrosis accelerating component 1710 may be used to eliminate or substantially reduce the incidence of infection through the formation of blood clots and wound healing.

Figure 18:
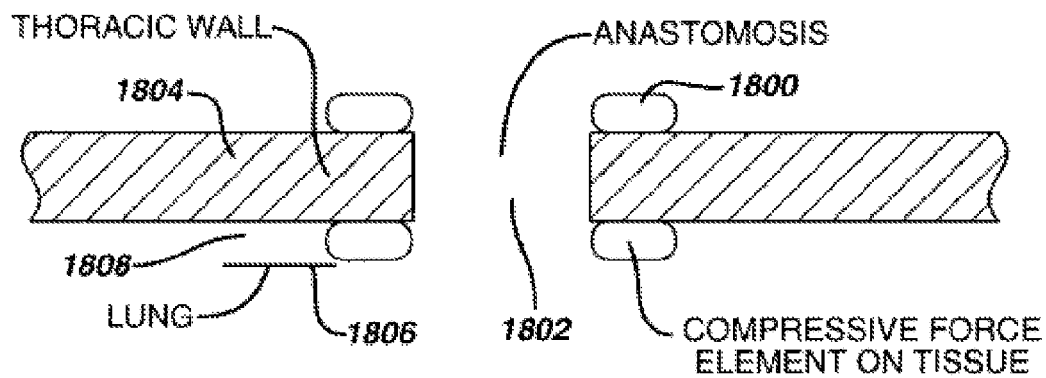
FIG. 18 is a diagrammatic representation of a second exemplary embodiment of a device for accelerating a fibrotic/wound healing response in accordance with the present invention.

In an alternate exemplary embodiment, a device for compressing the newly exposed bone and tissue surrounding the anastomosis may be utilized to accelerate a fibrotic/wound healing response. Referring to FIG. 18, there is illustrated an exemplary embodiment of a mechanical compression device 1800 for applying a substantially constant compressive force to at least a portion of, and preferably to all of the tissue surrounding the anastomosis 1802. The anastomosis 1802, as described above, is formed to create a passageway between the thoracic wall 1804 and the lung 1806. The pleurodesis may be formed in the pleural space 1808 by any of the devices and/or methods described herein. As illustrated, the mechanical compression device 1800 simply compresses the tissue forming the perimeter of the anastomosis 1802.

Figure 19:
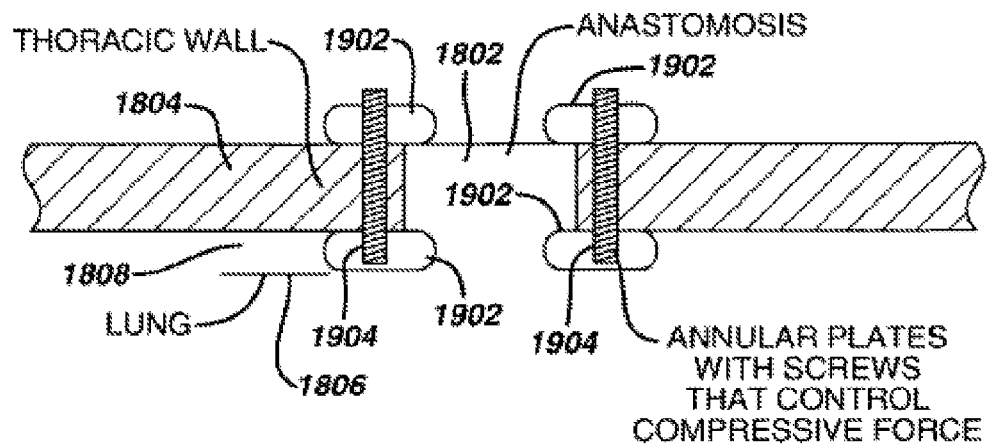
FIG. 19 is a diagrammatic representation of a third exemplary embodiment of a device for accelerating a fibrotic/wound healing response in accordance with the present invention.

The mechanical compression device 1800 may comprise any suitable means for applying a substantially compressive force. The mechanical compression device 1800 may be a permanent implant or temporary implant that may be easily removed after the anastomosis has healed. In addition, depending on the nature of the device, it may be formed from biodegradable or biosorbable materials. In one exemplary embodiment, the mechanical compression device 1800 may comprise an adjustable clamp 1900 as illustrated in FIG. 19. The clamp 1900 may comprise two annular plates 1902 connected by one or more set screws 1904 that maintain the annular plates 1902 spaced a predetermined distance apart. The set screws 1904 may be utilized to move the annular plates 1902 closer together or further apart depending on the desired compressive forces and the thickness of the anastomosis. The annular plates 1902 may be connected by springs or other means. In addition, the annular plates 1902 may be formed from magnetic materials and thus configured to attract one another to create the compressive forces.

Figure 20:
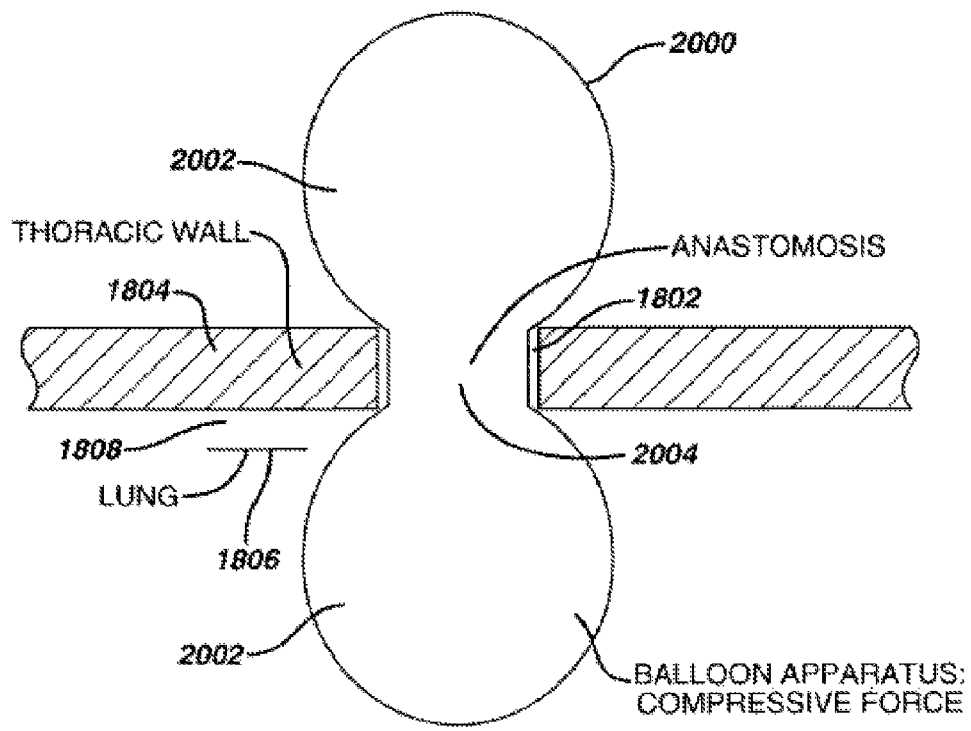
FIG. 20 is a diagrammatic representation of a fourth exemplary embodiment of a device for accelerating a fibrotic/wound healing response in accordance with the present invention.

In another exemplary embodiment, the mechanical compression device 1800 may comprise a balloon apparatus 2000 as illustrated in FIG. 20. In this exemplary embodiment, the balloon apparatus 2000 comprises two inflatable flanges 2002 interconnected by a single inflation tube 2004. The balloon apparatus 2000 may be positioned in the anastomosis 1802 (FIG. 18) with the uninflated flanges 2002 making contact with some and preferably all of the tissue surrounding the anastomosis 1802. Once in position, the flanges 2002 may be inflated until the desired compressive force is achieved.

In yet another alternate exemplary embodiment, the mechanical compression device 1800 may comprise an apparatus that utilizes a material prepared, treated or configured to apply a substantially constant compressive force. For example, a device may be formed from a material having super elastic or shape memory characteristics. Shape memory characteristics may be simplistically described as follows. A metallic structure, for example, a nitinol tube that is in an Austenite phase may be cooled to a temperature such that it is in the Martensite phase. Once in the Martensite phase, the nitinol tube may be deformed into a particular configuration or shape by the application of stress. As long as the nitinol tube is maintained in the Martensite phase, the nitinol tube will remain in its deformed shape. If the nitinol tube is heated to a temperature sufficient to cause the nitinol tube to reach the Austenite phase, the nitinol tube will return to its original or programmed shape. The original shape is programmed to be a particular shape by well-known techniques as briefly described above. Super elastic characteristics may be simplistically described as follows. A metallic structure, for example, a nitinol tube that is in an Austenite phase may be deformed to a particular shape or configuration by the application of mechanical energy. The application of mechanical energy causes a stress induced Martensite phase transformation. In other words the mechanical energy causes the nitinol tube to transform from the Austenite phase to the Martensite phase. By utilizing the appropriate measuring instruments, one can determine that the stress from the mechanical energy causes a temperature drop in the nitinol tube. Once the mechanical energy or stress is released, the nitinol tube undergoes another mechanical phase transformation back to the Austenite phase and thus its original or programmed shape. As described above, the original shape is programmed by well-known techniques. The Martensite and Austenite phases are common phases in many metals.

Figure 21:
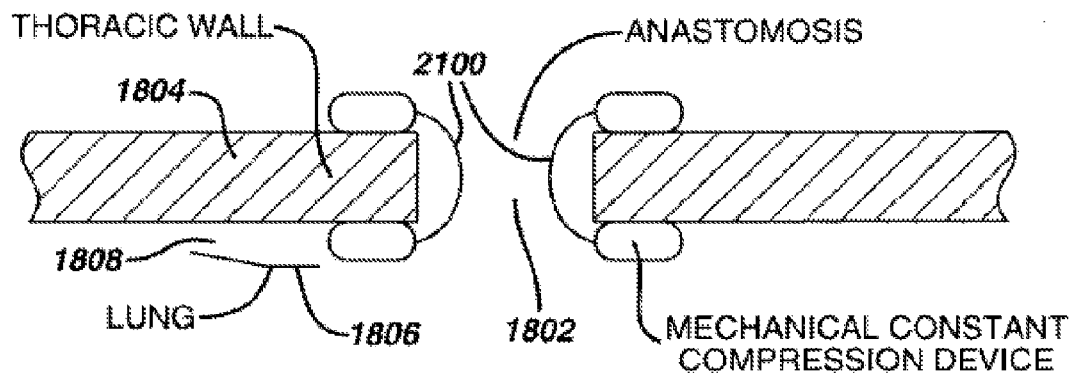
FIG. 21 is a diagrammatic representation of a fifth exemplary embodiment of a device for accelerating a fibrotic/wound healing response in accordance with the present invention.

Although nitinol is set forth in the description above, various metallic and non-metallic materials may be utilized. Referring to FIG. 21, there is illustrated a simple device 2100 for applying a substantially constant compressive force to the tissue surrounding the anastomosis. The device 2100 comprises a substantially hourglass design and may be formed from a material such as nitinol. The device 2100 may be designed from a plurality of interconnected struts or from a single piece of wire. The device 2100 may be compressed to a lower profile, through a restraining means, positioned in the anastomosis 1802 (FIG. 18) and then allowed to assume its programmed shape/configuration. If properly programmed, the device 2100 will preferably exert a chronic inward or compressive force.

In yet another alternate exemplary embodiment, a heat source may be utilized to accelerate fibrosis/wound healing. By contacting the tissue surrounding the anastomosis with a precisely controlled heat source, the wound healing process may be accelerated in a manner similar to the cauterization process utilized elsewhere in the body. Any suitable heat source may be utilized.

In each of the above-described exemplary embodiment, one or more drugs, agents, compounds for accelerating the fibrotic response, promoting wound healing and/or reducing the risk of infection may be utilized in conjunction with the specific device through controlled local delivery. For example, any number of drugs, agents and/or compounds may be releasably affixed to any of the above-described devices, with or without a polymeric coating.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

I claim:

1. A disposable and minimally invasive lung reduction device that allows air trapped in a lung to exit the lung other than through a natural airway of a patient, comprising:
    a first section including a conduit that is adapted to extend into and communicate with parenchymal tissue of the lung through an artificial air channel, wherein the artificial air channel enters the parenchymal tissue of the lung through an airtight seal of parietal and visceral pleurae of the lung; and
    a second section that is mounted on the chest wall external to the lung connecting to the conduit of the first section, the second section being larger than the first section such that when the second section mounted on the chest wall of a patient, the conduit of the first section extends into the parenchymal tissue of the lung and is held in that position,
    wherein the first section includes biocompatible materials that accelerate tissue healing and maintain the artificial air channel; and
    wherein air trapped in the lung can be expelled to the external environment of the lung through the artificial air channel.

2. The disposable and minimally invasive lung reduction device of claim 1 including a one-way valve located in the second section.

3. The disposable and minimally invasive lung reduction device of claim 1 wherein the second section includes a housing for an apparatus that draws air from a hyperinflated portion of the lung.

4. The disposable and minimally invasive lung reduction device of claim 3 wherein the apparatus includes one of a pump and a fan.

5. The disposable and minimally invasive lung reduction device of claim 1 including an apparatus that allows air trapped in the lung be expelled and does not allow air to re-enter the lung through the lung reduction device from the ambient environment.

6. The disposable and minimally invasive lung reduction device of claim 1 wherein the first section is configured to be minimally invasively placeable and removable through the artificial air channel.

7. A disposable and minimally invasive lung reduction device that allows air trapped in a lung to exit the lung other than through a natural airway of a patient, comprising:
    a first section including a conduit that is adapted to extend into and communicate with parenchymal tissue of the lung through an artificial air channel, wherein the artificial air channel enters the parenchymal tissue of the lung through an airtight seal of parietal and visceral pleurae of the lung;
    a second section that is mounted on the chest wall external to the lung connecting to the conduit of the first section the second section being larger than the first section such that when the second section mounted on the chest wall of a patient, the conduit of the first section extends into the parenchymal tissue of the lung and is held in that position; and
    a one way valve located in the second section,
    wherein the first section includes biocompatible materials that accelerate tissue healing and maintain the artificial air channel; and
    wherein air trapped in the lung can be expelled to the external environment of the lung through the artificial air channel.

8. The disposable and minimally invasive lung reduction device of claim 7 wherein the second section includes a housing for an apparatus that draws air from a hyperinflated portion of the lung.

9. The disposable and minimally invasive lung reduction device of claim 8 wherein the apparatus includes one of a pump and a fan.

10. The disposable and minimally invasive lung reduction device of claim 7 including an apparatus that allows air trapped in the lung be expelled and does not allow air to reenter the lung through the lung reduction device from the ambient environment.

11. The disposable and minimally invasive lung reduction device of claim 7 wherein the first section is configured to be minimally invasively placeable and removable through the artificial air channel.

12. The disposable and minimally invasive lung reduction device that allows air trapped in a lung to exit the lung other than through a natural airway of a patient, comprising:
    a first section including a conduit that is adapted to extend into and communicate with parenchymal tissue of the lung through an artificial air channel, wherein the artificial air channel enters the parenchymal tissue of the lung through an airtight seal of parietal and visceral pleurae of the lung;

a second section that is mounted on the chest wall external to the lung connecting to the conduit of the first section, the second section being larger than the first section such that when the second section mounted on the chest wall of a patient, the conduit of the first section extends into the parenchymal tissue of the lung and is held in that position, wherein the first section includes biocompatible materials that accelerate tissue healing and maintain the artificial air channel;

wherein the first section is configured to be minimally invasively placeable and removable through the artificial air channel; and wherein air trapped in the lung can be expelled to the external environment of the lung through the artificial air channel.

13. The disposable and minimally invasive lung reduction device of claim 12 including a one way valve located in the second section.

14. The disposable and minimally invasive lung reduction device of claim 12 wherein the second section includes a housing for an apparatus that draws air from a hyperinflated portion of the lung.

15. The disposable and minimally invasive lung reduction device of claim 14 wherein the apparatus includes one of a pump and a fan.

16. The disposable and minimally invasive lung reduction device of claim 12 including an apparatus that allows air trapped in the lung be expelled and does not allow air to reenter the lung through the lung reduction device from the ambient environment.

\* \* \* \* \*